US006849712B1

(12) United States Patent
McCarthy et al.

(10) Patent No.: US 6,849,712 B1
(45) Date of Patent: Feb. 1, 2005

(54) PEPTIDES WITH β1 INTEGRIN SUBUNIT DEPENDENT CELL ADHESION MODULATING ACTIVITY

(75) Inventors: James B. McCarthy, Minneapolis, MN (US); Leo T. Furcht, Minneapolis, MN (US); Angela Brienzo Frey, Waukesha, WI (US)

(73) Assignee: Regents of the University of Minnesota, Minneapolis, MN (US)

( * ) Notice: Subject to any disclaimer, the term of this patent is extended or adjusted under 35 U.S.C. 154(b) by 0 days.

(21) Appl. No.: 09/600,432

(22) PCT Filed: Jan. 21, 1999

(86) PCT No.: PCT/US99/01236

§ 371 (c)(1),
(2), (4) Date: Oct. 2, 2000

(87) PCT Pub. No.: WO99/37669

PCT Pub. Date: Jul. 29, 1999

Related U.S. Application Data
(60) Provisional application No. 60/096,212, filed on Aug. 12, 1998, provisional application No. 60/096,211, filed on Aug. 12, 1998, and provisional application No. 60/072,119, filed on Jan. 22, 1998.

(51) Int. Cl.$^7$ ................................................ C07K 7/06
(52) U.S. Cl. ........................... 530/329; 514/15; 514/16; 514/17; 514/18; 530/327; 530/328
(58) Field of Search ..................... 514/15–19; 530/329, 530/330, 331, 327, 328

(56) References Cited

U.S. PATENT DOCUMENTS

| | | | |
|---|---|---|---|
| 4,505,853 A | * 3/1985 | Goldstein et al. | ........... 530/301 |
| 5,116,368 A | 5/1992 | McCarthy et al. | ............. 623/2 |
| 5,359,048 A | * 10/1994 | Ohba et al. | ............. 536/23.71 |
| 5,382,569 A | 1/1995 | Cody et al. | .................... 514/17 |
| 5,731,409 A | 3/1998 | Fields et al. | ................ 530/324 |
| 6,013,628 A | 1/2000 | Skubitz et al. | ................ 514/12 |

FOREIGN PATENT DOCUMENTS

| | | |
|---|---|---|
| EP | 347 890 B1 | 12/1989 |
| EP | 0 347 890 A1 | 12/1989 |
| EP | 576 898 A3 | 1/1994 |
| EP | 0 576 898 A2 | 1/1994 |
| WO | 008806039 * | 8/1988 |
| WO | WO 89/01942 | 3/1989 |
| WO | WO 93/17047 | 9/1993 |
| WO | WO 94/17097 | 8/1994 |
| WO | WO 00/56350 A3 | 9/2000 |

OTHER PUBLICATIONS

Newsholme, Journal of Biological Chemistry 267(2), 810–18, 1992.*

Westerlink, Proc Natl Acad Sci 92, 4–21, 1995.*

Fields et al., "Chapter 3: Principles and Practice of Solid–Phase Peptide Synthesis," *Synthetic Peptides: A User's Guide*, Grant, ed., W. H. Freeman & Co., New York, title page, publication page, table of contents, and pp. 77–183 (1992).

Furcht et al., "Editorial: Tumor Cell Invasion, Matrix Metalloproteinases, and the Dogma," *Laboratory Investigation*, 70(6):781–783 (1994).

Guan et al., "Lymphoid Cells Recognize an Alternatively Spliced Segment of Fibronectin via the Integrin Receptor $\alpha_4\beta_1$," *Cell*, 60(1):53–61 (1990).

Guo et al., "Fibronectin Peptide (FN C/H V–Y) Assay and Stability in Human and Rat Plasma," Abstract 4029, American Association of Pharmaceutical Scientists Annual Meeting, Nov. 14–18, New Orleans, LA (1999).

Hallenbeck et al., "Polymorphonuclear Leukocyte Accumulation in Brain Regions with Low Blood Flow During the Early Postischemic Period," *Stroke*, 17(2):246–253 (1986).

Hines et al., "Synthetic fibronectin peptides interrupt inflammatory cell infiltration in transforming growth factor β1 knockout mice," *Proceedings of the National Academy of Sciences, USA*, 91(11):5187–5191 (1994).

Huebsch et al., "Endothelial Cell Interactions With Synthetic Peptides From the Carboxyl–Terminal Heparin–Binding Domains of Fibronectin," *Circulation Research*, 77(1):43–53 (1995).

Humphries et al., "A Synthetic Peptide from Fibronectin Inhibits Experimental Metastasis of Murine Melanoma Cells," *Science*, 223(4762):467–470 (1986).

Hynes, "Integrins: A Family of Cell Surface Receptors," *Cell*, 48(4):549–554 (1987).

Iida et al., "Coordinate Role for Cell Surface Chondroitin Sulfate Proteoglycan and α4β1 Integrin in Mediating Melanoma Cell Adhesion to Fibronectin," *The Journal of Cell Biology*, 118(2):431–444 (1992).

Jackson et al., "Potent α4β1 Peptide Antagonists as Potential Anti–Inflammatory Agents," *Journal of Medicinal Chemistry*, 40(21):3359–3368 (1997).

Johnson, "8. The Cutaneous Circulation," *Laser–Doppler Blood Flowmetry*, Shepherd et al., eds., Kluver Academic Publishers, Norwell, MA, Title page, publication page, and pp. 121–139 (1990).

(List continued on next page.)

Primary Examiner—Jon P. Weber
Assistant Examiner—David Lukton
(74) Attorney, Agent, or Firm—Mueting Raasch & Gebhardt, P.A.

(57) ABSTRACT

Peptides capable of modulating β1 integrin subunit dependent cell adhesion which includes a C-terminal aromatic amino acid residue and an amino acid residue having a lipophilic alkyl side chain as the penultimate C-terminal residue are provided. These "LipAr" C-terminated peptides are typically capable of modulating the β1 integrin subunit dependent adhesion of cells, such as Ramos cells.

27 Claims, 19 Drawing Sheets

OTHER PUBLICATIONS

Kochanek et al., "Polymorphonuclear Leukocytes and Monocytes/Macrophages in the Pathogenesis of Cerebral Ischemia and Stroke," *Stroke*, 23(9):1367–1379 (1992).

Lasky, "Selectins: Interpreters of Cell–Specific Carbohydrate Information During Inflammation," *Science*, 258(5084):964–969 (1992).

Lauer et al., "Inhibition of Melanoma Cell Binding to Type IV Collagen by Analogs of Cell Adhesion Regulator," *Journal of Medicinal Chemistry*, 40(19):3077–3084 (1997).

Levrey et al., "Induction of Fibroblast Apoptosis by Soluble Fibronectin Peptides," Abstract 1050, 37th Annual Meeting of the American Society for Cell Biology, Dec. 13–17, 1997, Washington, D.C., *Molecular Biology of the Cell*, 8:181A (Nov., 1997).

Lobb et al., "Small molecule antagonists of $\alpha 4$ integrins: novel drugs for asthma," *Exp. Opin. Invest. Drugs*, 8(7):935–945 (Jul., 1999).

Madden et al., "A peptide derived from neutrophil inhibitory factor (NIF) blocks neutrophil adherence to endothelial cells," *Inflammation Research*, 46(6):216–223 (1997).

Matsuo et al., "Role of Neutrophils in Radical Production During Ischemia and Reperfusion of the Rat Brain: Effect of Neutrophil Depletion on Extracellular Ascorbyl Radical Formation," *Journal of Cerebral Blood Flow and Metabolism*, 15(6):941–947 (1995).

McCarthy et al., "Laminin and Fibronectin Promote the Haptotactic Migration of B16 Mouse Melanoma Cells In Vitro," *The Journal of Cell Biology*, 98(4):1474–1480 (1984).

McCarthy et al., The role of cell adhesion proteins—laminin and fibronectin—in the movement of malignant and metastatic cells, *Cancer and Metastatis Reviews*, 4(2):125–152 (1985).

Norgard–Sumnicht et al., "Calcium–Dependent Heparin––Like Ligands for L–Selectin in Nonlymphoid Endothelial Cells," *Science*, 261(5120):480–483.

Parker et al., "New Hydrophilicity Scale Derived from High–Performance Liquid Chromatography Peptide Retention Data: Correlation of Predicted Surface Residues with Antigenicity and X–ray–Derived Accessible Sites," *Biochemistry*, 25(19):5425–5432 (1986).

Prosper et al., "Mobilization and Homing of Peripheral Blood Progenitors Is Related to Reversible Downregulation of $\alpha 4 \beta 1$ Integrin Expression and Function," *The Journal of Clinical Investigation*, 101(11):2456–2467 (1998).

Radzicka et al., "Comparing the Polarities of the Amino Acids: Side–Chain Distribution Coefficients between the Vapor Phase, Cyclohexane, 1–Octanol, and Neutral Aqueous Solution," *Biochemistry*, 27(5):1664–1670 (1988).

Ruoslahti, "Integrins," *The Journal of Clinical Investigation*, 87(1):1–5 (1991).

Springer, "Adhesion receptors of the immune system," *Nature*, 346(6283):425–434 (1990).

Springer, "Folding of the N–terminal, ligand–binding region of integrin $\alpha$–subunits into a $\beta$–propeller domain," *Proceedings of the National Academy of Sciences USA*, 94(1):65–72 (1997).

Wahl et al., "Synthetic Fibronectin Peptides Suppress Arthirits in Rats by Interrupting Leukocyte Adhesion and Recruitment," *The Journal of Clinical Investigation*, 94(2):655–662 (1994).

Weiss, "Tissue Destruction by Neutrophils," *The New England Journal of Medicine*, 320(6):365–376 (1989).

Woods et al., "A Synthetic Peptide from the COOH–Terminal Heparin–binding Domain of Fibronectin Promotes Focal Adhesion Formation," *Molecular Biology of the Cell*, 4(6):605–613 (1993).

Cue et al., "A nonpeptide integrin antagonist can inhibit epithelial cell ingestion of *Streptococcus pyogenes* by blocking formation of integrin alpha 5beta 1–fibronectin–M1 protein complexes," *Proceedings of the National Academy of Sciences, USA*, 97(6):2858–63 (2000).

Duan et al., "Enhancement of nigral graft survival in rat brain with the systemic administration of synthetic fibronectin peptide V," *Neuroscience*, 100(3):521–30 (2000).

Humphries et al., "An Anthropomorphic Integrin," *Science*, 294(5541):316–7 (2001).

Lasky, "How Integrins Are Activated," *Nature*, 390(6655):15, 17 (1997).

Lenter et al., "A Monoclonal Antibody Against an Activation Epitope on Mouse Integrin Chain $\beta_1$ Blocks Adhesion of Lymphocytes to the Endothelial Integrin $\alpha_6 \beta_1$," *Proceedings of the National Academy of Sciences, USA*, 90(19):9051–9055 (1993).

McCarthy et al., "Human monocyte binding to fibronectin enhances IFN–gamma–induced early signaling events," *The Journal of Immunology*, 159(5):2424–30 (1997).

Xiong et al., "Crystal Structure of the Extracellular Segment of Integrin $\alpha V \beta 3$," *Science*, 294(5541):339–45 (2001).

Hogg et al., "The sticking point: how integrins bind to their ligands," *Trends in Cell Biology*, 4:379–382 (1994).

Huhtala et al., "Cooperative Signaling by $\alpha 5 \beta 1$ and $\alpha 4 \beta 1$ Integrins Regulates Metalloproteinase Gene Expression in Fibroblasts Adhering to Fibronectin," *The Journal of Cell Biology*, 129(3):867–879 (1995).

Humphries, "Integrin activation: the link between ligand binding and signal transduction," *Current Opinion in Cell Biology*, 8(5):632–640 (1996).

Irie et al., "Critical amino acid residues for ligand binding are clustered in a predicted $\beta$–turn of the third N–terminal repeat in the integrin $\alpha 4$ and $\alpha 5$ subunits," *The EMBO Journal*, 14(22):5550–5556 (1995).

Irie et al., "Multiple loop structures critical for ligand binding of the integrin $\alpha 4$ subunit in the upper face of the $\beta$–propeller mode 1," *Proceedings of the National Academy of Sciences USA*, 94(14):7198–7203 (1997).

Isberg et al., "Multiple $\beta_1$ Chain Integrins Are Receptors for Invasin, a Protein That Promotes Bacterial Penetration into Mammalian Cells," *Cell*, 60(5):861–871 (1990).

Leong et al., "Identification of the integrin binding domain of the *Yersinia pseudotuberculosis* invasin protein," *The EMBO Journal*, 9(6):1979–1989 (1990).

Loftus et al., "Integrin–mediated Cell Adhesion: The Extracellular Face," *The Journal of Biological Chemistry*, 269(41):25235–25238 (1994).

Mooradian et al., "Characterization of FN–C/H–V, a Novel Synthetic Peptide From Fibronectin That Promotes Rabbit Corneal Epithelial Cell Adhesion, Spreading, and Motility," *Investigative Opthalmology & Visual Science*, 34(1):153–164 (1993).

O'Toole et al., "Regulation of Integrin Affinity States through an NPXY Motif in the $\beta$ Subunit Cytoplasmic Domain," *The Journal of Biological Chemistry*, 270(15):8553–8558 (1995).

Pujades et al., "Defining Extracellular Integrin α–Chain sites That Affect Cell Adhesion and Adhesion Strengthening without Altering Soluble Ligand Binding," *Molecular Biology of the Cell*, 8(12):2647–2657 (1997).

Scallon et al., "Primary Structure and Functional Activity of a Phosphatidylinositol–Glycan–Specific Phospholipase D," *Science*, 252(5004):446–448 (1991).

Takada et al., "Identification of a Regulatory Region of Integrin $\beta_1$ Subunit Using Activating and Inhibiting Antibodies," *The Journal of Biological Chemistry*, 268(23):17597–17601 (1993).

Takada et al., "Structural Basis of Integrin–Mediated Signal Transduction," *Matrix Biology*, 16(4):143–151 (1997).

Tuckwell et al., "A Secondary Structure Model of the Integrin α Subunit N–Terminal Domain Based on Analysis of Multiple Alignments," *Cell Adhesion and Communication*, 2(5):385–402 (1994).

Wilke et al., "Human Keratinocytes Adhere to and Spread on Synthetic Peptide FN–C/H–V Derived from Fibronectin," *The Journal of Investigative Dermatology*, 101(1):43–48 (1993).

Lasz et al., "62 $_3$ Integrin Derived Peptide 217–230 Inhibits Fibrinogen Binding and Platelet Aggregation: Significance of RGD Sequences and Fibrinogen Aα–Chain," *Biochemical and Biophysical Research Communications*, 190(1):118–124 (1993).

Adelsman et al., "Stimulation of β1–Integrin Function by Epidermal Growth Factor and Heregulin–β Has Distinct Requirements for erbB2 but a Similar Dependence on Phosphoinositide 3–OH Kinase," *Molkecular Biology of the Cell*, 10(9):2861–2878 (Sep., 1999).

Akiyama et al., "Fibronectin" *Advances in Enzymology and Related Areas of Molecular Biotechnology*, vol. 59, Meister, ed., John Wiley and Sons, New York, Title page, publication page, and pp. 1–57 (1987).

Boykin et al., "In Vivo Microcirculation of a Scald Burn and the Progression of Postburn Dermal Ischemia," *Plastic and Reconstructive Surgery*, 66(2):191–198 (1980).

Brienzo, *Identification of a novel anti–adhesion integrin––binding motif within a fibronectin synthetic peptide*, PhD Thesis, University of Minnesota, 120 pages (1998).

Bruck et al., "The Use of Synthetic Analogues of Arg–Gly–Asp (RGD) and Soluble Receptor of Tumor Necrosis Factor to Prevent Acute and Chronic Experimental Liver Injury," *Yale Journal of Biology and Medicine*, 70(4):391–402 (1997).

Carrico et al., "Chapter 12: Transfusion, Autotransfusion, and Blood Substitutes," *Trauma*, 4$^{th}$ ed., Mattox et al., eds., McGraw–Hill Co., Inc., United States, Publication page and pp. 233–243 (2000).

Yanaka et al., "Synthetic fibronectin peptides and ischemic brain injury after transietn middle cerebral artery occlusion in rats," *Journal of Neurosurgery*, 85(1):125–130 (1996).

Yanaka et al., "Neuronal Protection from Cerebral Ischemia by Synthetic Fibronectin Peptides to Leukocyte Adhesion Molecules," *Journal of Cerebral Blood Flow and Metabolism*, 16(6):11210–1125 (1996).

Yanaka et al., "Antagonism of Leukocyte Adherence by Synthetic Fibronectin Peptide V in a Rat model of Transient Focal Cerebral Ischemia," *Neurosurgery*, 40(3)557–563 (1977).

McCarthy et al., "Human Fibronectin Contains Distinct Adhesion–and Motility–promoting Domains for Metastic Melanoma Cells," *The Journal of Cell Biology*, 102(1):179–188 (1986).

McCarthy et al., "Localization and Chemical Synthesis of Fibronectin Peptides with Melanoma Adhesion and Heparin Binding Activities," *Biochemistry*, 27(4):1380–1388 (1988).

McCarthy et al., "Metastasis Inhibition of Different Tumor Types by Purified Laminin Fragments and a Heparin–Binding Fragment of Fibronectin," *Journal of the National Cancer institute*, 80(2):108–116 (1988).

McCarthy et al., "RGD–Independent Cell Adhesion to the Carboxy–terminal Heparin–binding Fragment of Fibronectin Involves Heparin–dependent and–independent Activities," *The Journal of Cell Biology*, 110(3):777–787 (1990).

McCarthy et al., "Tumor cell adhesive mechanisms and their relationship to metastasis," *Seminars in Cancer Biology*, 2(3):155–167 (1991).

McCartney–Francis et al,, "Autoimmune Sjögren's–Like Lesions in Salivary Glands of TGF–β1–Deficient Mice Are inhibited by Adhesion–Blocking Peptides," *The Journal of Immunology*, 157(3):1306–1312 (1996).

McCartney–Francis et al., "Lacrimal Gland Inflammation Is Responsible for Ocular Pathology in TGF–β1 Null Mice," *American Journal of Pathology*, 15(5):1281–1288 (1997).

Mileski et al., "Streptococcus Pneumonaie—Stimulated Macrophages Induce Neutrophils to Emigrate by a CD18–Independent Mechanism of Adherence," *Circulatory Shock*, 31(3):259–267 (1990).

Mileski et al., "Inhibition of Leukocyte–Endothelial Adherence Following Thermal Injury," *Journal of Surgical Research*, 52(4):334–339 (1992).

Mileski et al., "The Accuracy of Burn Wound Assessment by Laser Doppler Flowmetry is Improved by Serial Measurements," Abstract 31, 31$^{st}$ Annual Meeting, American Burn Association, Mar. 24–27, Lake Buena Vista, FL, (Mar. 1999).

Mohri, "Interaction of Fibronectin With Integrin Receptors: Evidence by Use of Synthetic Peptides," *Peptites*, 18(6):899–907 (1997).

Moyle et al., "A Hookworm Glycoprotein That inhibits Neutrophil Function Is a Ligand of the Integrin CD11b/CD18," *The Journal of Biological Chemistry*, 269(13):10008–10015 (1994).

American Type Culture Collection, "ATCC No. 25923," organism:*Staphylcoccus aureus*; designation: Seattle 1945 [online]; Manassas, VA [retrieved on Feb. 6, 2002] from the Internet. Retrieved from the Internet: <URL:http://phage.atcc.org/cgi–bin/searchengine/longview.cgi?view=ba, 4359370,25923&text=25923>, 3 pages.

* cited by examiner

US 6,849,712 B1

PEPTIDES WITH β1 INTEGRIN SUBUNIT DEPENDENT CELL ADHESION MODULATING ACTIVITY

CROSS-REFERENCED TO RELATED APPLICATIONS

The present application is a national stage filing of International Patent Application No. PCT/US99/01236, filed on Jan. 21, 1999, which in turn is an international filing of U.S. provisional application Ser. No. 60/072,119 filed on 22 Jan. 1998, entitled "Peptides with Beta Integrin Subunit Dependent Cell Adhesion Modulating Activity"; U.S. provisional application Ser. No. 60/096,212 filed on 12 Aug. 1998 entitled "Peptides with β1 Integrin Subunit Dependent Cell Adhesion Modulating Activity"; and U.S. provisional application Ser. No. 60/096,211 filed on 12 Aug. 1998 entitled "Peptides with β1 Integrin Subunit Dependent Cell Adhesion Modulating Activity", the disclosures of which are herein incorporated by reference.

BACKGROUND OF THE INVENTION

Cellular recognition of the extracellular matrix ("ECM") proteins and of other cells has a complex molecular basis, involving multiple distinct cell surface receptors. Integrins are a family of receptors that are fundamentally important for mediating cell adhesion to ECM proteins. Tumor cells adhere to variety of ECM proteins and molecules on other cells as they invade and metastasize. These interactions of tumor cells have a profound effect on their phenotype. Although its exact role is complex and not completely understood, α4β1 integrin has been implicated in tumor cell arrest and/or extravasation and is involved in tumor cell invasion and metastasis. This integrin is expressed on many hematopoietic malignancies and also on tumors such as melanomas. α4β1 integrin is unique among integrins in that it binds to both ECM components (e.g. fibronectin) and Ig superfamily adhesion receptors (e.g., VCAM-1) which are expressed on activated endothelial cells and other cell types. α4β1 integrin also binds to itself and promotes homotypic cell adhesion. Although a role for α4β1 integrin has been established in modulating various aspects of tumor cell biology, the mechanisms by which the function of the α4β1 integrin is modulated are complex and not well understood. Understanding the nature of such interactions may help to explain cell-type specific behavior on ECM proteins that are often observed with integrins. There is, accordingly, a continuing need to identify peptides capable of modulating α4β1 dependent cell adhesion as a means of furthering the understanding of the complex interactions involving this integrin.

SUMMARY OF THE INVENTION

The present invention relates to peptides capable of modulating β1 integrin subunit dependent cell adhesion. The peptides include a C-terminal amino acid residue having a side chain which includes an aromatic group ("—Ar—") and an amino acid residue with a lipophilic alkyl side chain group ("—Lip—") as the penultimate C-terminal residue. This C-terminal dipeptide sequence is referred to herein as a "LipAr motif." For example, suitable peptides of the invention may include a C-terminal tyrosine residue and an isoleucine residue as the penultimate C-terminal residue, i.e., a C-terminal "IY motif" (Ile-Tyr). While the present peptides may include a relatively large number of amino acid residues, e.g., up to about 100 amino acid residues or more, as disclosed herein even very small peptides which include the LipAr motif, such as the dipeptide Ile-Tyr and the tripeptide Arg-Ile-Tyr, are capable of modulating β1 dependent adhesion. The present peptides typically have no more than about 50 and, preferably, no more than about 25 amino acid residues. The LipAr C-terminated peptides are preferably capable of inhibiting the β1 integrin subunit dependent adhesion of cells, such as the α4β1 integrin dependent adhesion of Ramos cells and the α5β1 integrin dependent adhesion of erythroleukemic cells (e.g., the erythroleukemic cell line K562).

DETAILED DESCRIPTION OF THE INVENTION

Figure 1:
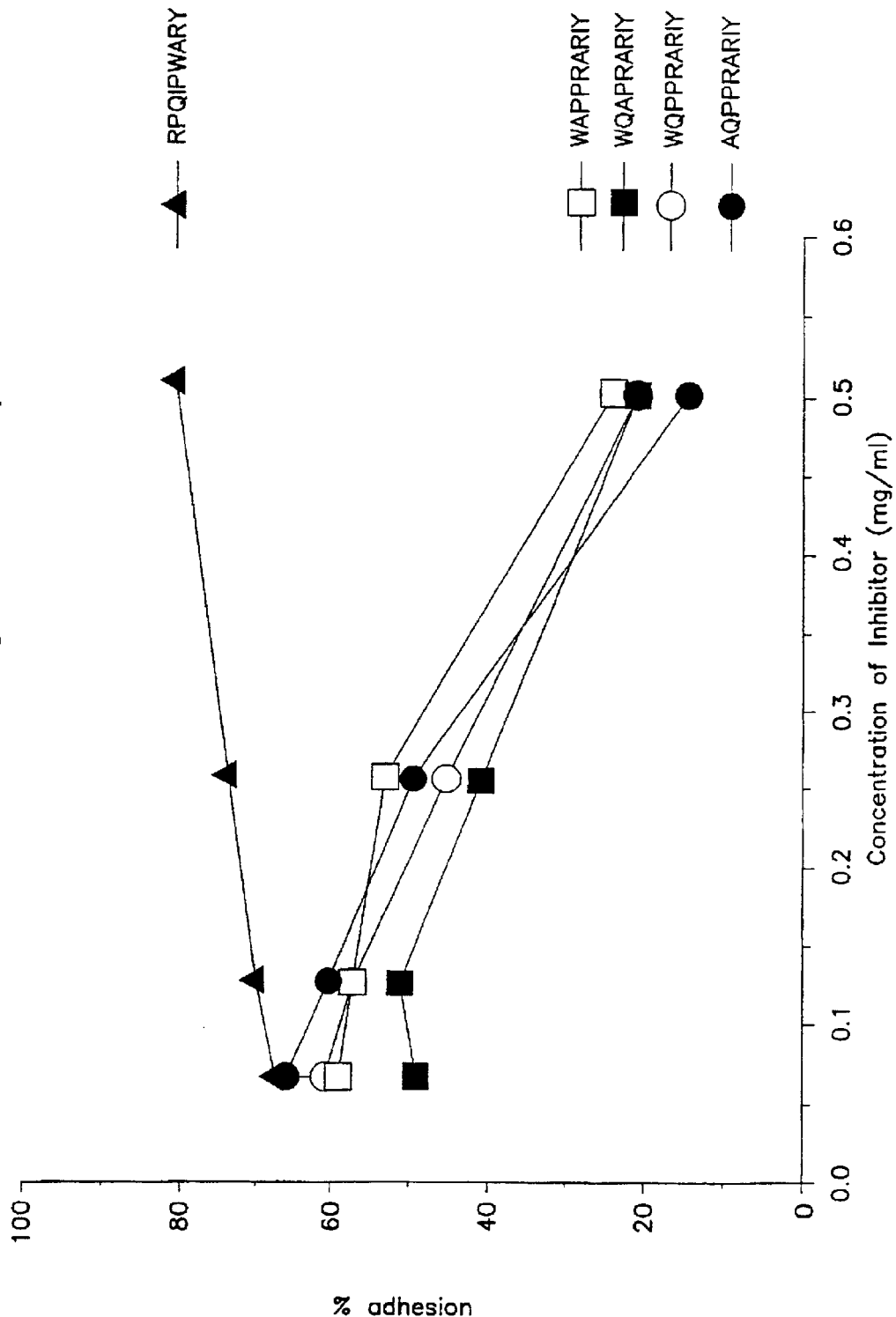
FIG. 1 shows a graph of % adhesion of 8A2 stimulated Ramos cells to IIICS-GST as a function of the concentration of a number of alanine knockout analogs of FN-C/H V+Y. FN C/H V+Y and a scrambled variant lacking a C-terminal IY motif ("sV"; RPQIPWARY (SEQ ID NO:2)) were included as controls.

The present invention relates to peptides capable of modulating β1 integrin subunit dependent cell adhesion. These peptides include a C-terminal LipAr motif and are typically capable of inhibiting β1 integrin subunit dependent cell adhesion and, in particular, of inhibiting α4β1 integrin dependent cell adhesion. The present peptides typically are also capable of inhibiting α2β1, α3β1 and/or α5β1 integrin dependent cell adhesion. As used herein, the term "LipAr motif" refers to a dipeptide sequence in which C-terminal "Ar" residue has a side chain which includes an aromatic group. Examples of suitable amino acid residues having an aromatic group include tyrosine ("Tyr"), phenylalanine ("Phe"), histidine ("His"), and tryptophan ("Trp"). The penultimate C-terminal "Lip" residue is an amino acid residue which includes a lipophilic alkyl side chain group. The α-carboxyl group of the C-terminal amino acid residue of the present peptides is typically in the form of a carboxylic acid ($-CO_2H$). In a preferred embodiment of the invention, the "Lip" and "Ar" residues are L-amino acid residues.

Examples of amino acid residues which have a lipophilic alkyl side chain group include leucine ("Leu"), isoleucine ("Ile"), and valine ("Val"). Typically, the lipophilic alkyl side chain group has a SCDC (cyclohexane-water side chain distribution coefficient calculated as $-RT \ln K_D$ and expressed in kcal/mol) of at least about 3.0 and, preferably, at least about 4.0. For the purposes of this application, SCDC is defined according to Radzicka et al., *Biochemistry*, 27, 1664 (1988). Where the SCDC of a particular alkyl side chain group is not known, the SCDC value may be determined by measurement of the distribution coefficient between wet cyclohexane and water or by a comparison of a compound containing the same alkyl side chain group with other similar compounds using a hydrophobicity scale derived from HPLC retention according to the method of Parker et al., *Biochernistry*, 25, 5425 (1986). Despite its similarity in some respects to lipophilic alkyl side chain groups such as leucine, isoleucine, and valine, insertion of a methionine residue at the penultimate position (i.e., an "MY" C-terminal motif) resulted in an inactive analog.

Four C-terminal tyrosine tagged peptides having sequences corresponding to different fragments of the fibronectin C-terminal heparin binding domain have been reported to inhibit the binding of peripheral blood mononuclear cells and spleen cells to fibronectin and endothelial cell monolayers (see, e.g., Wahl et al., J. Clin. Invest.,; 24, 655–662 (1994)). Two of these peptides, FN-C/H I+Y and FN-C/H V+Y, contain a C-terminal LipAr motif. The amino acid sequence of FN-C/H I+Y is YEKPGSPPREV-VPRPRPGVY (SEQ ID NO:42). The amino acid sequence of FN-C/H V+Y is WQPPRARIY (SEQ ID NO:1). The other two Tyr-tagged fibronectin C-terminal heparin binding domain related peptides do not contain a C-terminal LipAr motif (both peptides end in "TY" (Thr-Tyr)). The amino acid sequences of the these other two fibronectin C-terminal heparin binding domain fragments are KNNQKSEPLIGR-KKTY (FN-C/H II+Y; (SEQ ID NO:43)), and SPPRRARVTY (FN-C/H IV+Y; (SEQ ID NO:44)), Although all four Y-tagged fragments inhibit leukocyte adhesion to fibronectin in vitro, only three of the four, FN-C/H I+Y, FN-C/H II+Y and FN-C/H V+Y, are reported to exhibit anti-inflammatory properties in an in vivo rat model. One of the four, FN-C/H V+Y, has also been reported to have to inhibit adhesion to VCAM, another extracellular matrix protein. The reported results suggest that the biological activity of the Y-tagged fibronectin C-terminal heparin binding domain fragments is a functional of the specific sequence of each of the peptides.

Several analogs were prepared to examine whether the inhibition of the β1 integrin dependent cell adhesion is effected by the chirality of the inhibitor. The all D-form of FN-C/H V+Y (SEQ ID NO:1) and the all L-form of retro inverso FN-C/H V+Y (SEQ ID NO:40; the all L-form of YIRARPPQW, the reverse primary sequence of FN-C/H V+Y) were prepared and examined in the 8A2stimulated Ramos cell adhesion assay. Neither of these two compounds inhibited Ramos cell binding, suggesting that the present peptides preferably include the C-terminal LipAr motif in the form of L-enantioneric amino acid residues.

It has surprisingly been discovered, however, that the alanine knockout analogs of FN-C/H V+Y which preserve the C-terminal LipAr motif (i.e., retain the C-terminal Ile-Tyr dipeptide sequence) are capable of inhibiting β1 integrin dependent cell adhesion. As used herein, the term "alanine knockout analog" refers to an analog of a peptide in which a single residue has been substituted by an alanine residue.

Two of the alanine knockout analogs of FN-C/H V+Y have an alanine residue substituted for one of the arginine residues in the "PRARI" motif (Pro-Arg-Ala-Arg-Ile (SEQ ID NO:39)) within FN-C/H V+Y which has previously demonstrated to be the implicated in stimulated focal contact formation (see, e.g., Woods et al., Molec. Biol. Cell, 4, 605–613 (1993)). These alanine knockout analogs have the amino acid sequences WQPPRAAIY (SEQ ID NO:8) and WQPPAARIY (SEQ ID NO:17). Two of the other alanine knockout analogs, AQPPRARIY (SEQ ID NO:3), WAPPRARIY (SEQ ID NO:4), also differ from FN-C/H V+Y by a non-conservative amino acid substitution (Ala for Trp and Ala for Gln respectively).

As the examples described herein demonstrate, peptides which differ from FN-C/H V+Y by a non-conservative amino acid substitution but retain the C-terminal LipAr motif can be capable of modulating β1 integrin subunit dependent cell adhesion even if the overall physical properties of the peptide differ substantially from FN-C/H V+Y. For example, an FN-C/H V+Y analog in which the two arginine residues have been replaced by aspartic acid residues inhibits the 8A2 stimulated adhesion of Ramos cells at least as strongly as FN-C/H V+Y. The analog, WQPPDADIY (SEQ ID NO:38), exhibits this activity even though it has an overall net charge of −2 (in contrast to the +2 net charge of FN-C/H V+Y).

Even more surprising than the fact that non-conservative substitution variants of FN-C/H V+Y retain the capability of inhibiting β1 integrin subunit dependent cell adhesion, is the fact that other short Lip Ar C-terminated peptides with little or no sequence homology to FN-C/H V+Y also possess this type of biological activity. The results disclosed herein establish that even peptides with less than 50% homology with the corresponding C-terminal portion of FN-C/H V+Y or FN-C/H I+Y exhibit the capability of inhibiting β1 integrin subunit dependent adhesion. Examples of such peptides include ARITGYIIY (SEQ ID NO:14), RARITGYIY (SEQ ID NO:13), PRQAWRPIY (SEQ ID NO:18), and RPAPQRWIY (SEQ ID NO:20).

As used herein, the term "% homology" refers to the percentage of amino acid residues of a peptide which are either identical to that of an original peptide sequence or differ from the original peptide sequence solely as a result of a conservative amino acid substitution. For example, the peptide PAIFDRSCGS (SEQ ID NO:41) has 40% identity and 80% homology with respect to the peptide sequence PKVMERTCDS (SEQ ID NO:45).

For the purposes of this invention, conservative amino acid substitutions are defined to result from exchange of amino acids residues from within one of the following classes of residues: Class I: Ala, Gly, Ser, Thr, and Pro (representing small aliphatic side chains and hydroxyl group side chains); Class II: Cys, Ser, Thr and Tyr (representing side chains including an —OH or —SH group); Class III: Glu, Asp, Asn and Gln (carboxyl group containing side chains): Class IV: His, Arg and Lys (representing basic side chains); Class V: Ile, Val, Leu, Phe and Met (representing hydrophobic side chains); and Class VI: Phe, Trp, Tyr and His (representing aromatic side chains). The classes also include related amino acids such as 3Hyp and 4Hyp in Class I; homocysteine in Class II; 2-aminoadipic acid, 2-aminopimelic acid, γ-carboxyglutamic acid, β-carboxyaspartic acid, and the corresponding amino acid amides in Class III; ornithine, homoarginine, N-methyl lysine, dimethyl lysine, trimethyl lysine, 2,3-diaminopropionic acid, 2,4-diaminobutyric acid, homoarginine, sarcosine and hydroxylysine in Class IV; substituted phenylalanines, norleucine, norvaline, 2-aminooctanoic acid, 2-aminoheptanoic acid, statine and β-valine in Class V; and naphthylalanines, substituted phenylalanines, tetrahydroisoquinoline-3-carboxylic acid, and halogenated tyrosines in Class VI.

In another embodiment of the present invention, the peptides contain no more than 10 amino acid residues and have a sequence which does not correspond substantially to the amino acid sequence of FN-C/H V+Y. As used herein, the sequence of a particlar peptide does not correspond substantially to a reference amino acid sequence, if the particular peptide sequence has less than about 80% identity and preferably less than about 50% homology with the reference sequence.

One group of particularly suitable peptides of the invention are those which include a C-terminal "IIY" motifs i.e., the sequence of the three C-terminal most amino acid residues is Ile-Ile-Tyr. One such peptide contains 9 amino acid residues and has the sequence ARITGYIIY (SEQ ID NO:14).

From a variety of standpoints, including cost, ease of production and overal efficiency, smaller versions of the present peptides can offer many distinct advantages. Thus, one group of particularly advantageous peptides of the invention include the C-terminal IY motif and contain no more than ten and, preferably, no more than six amino acid residues. In addition to the dipeptide Ile-Tyr, suitable examples of this group include PRARIY (SEQ ID NO:24), RARIY (SEQ ID NO:25), ARIY (SEQ ID NO:26) and RIY.

Synthesis of Peptides

The peptides of the invention may be synthesized by the solid phase method using standard methods based on either t-butyloxycarbonyl (BOC) or 9-fluorenylmethoxy-carbonyl (FMOC) protecting groups. This methodology is described by G. B. Fields et al. in *Synthetic Peptides: A User's Guide*, W. M. Freeman & Company, New York, N.Y., pp. 77–183 (1992), the disclosure of which is herein incorporated by reference. Peptide structures and purity can be analyzed by HPLC, and amino acid analysis and sequencing.

The present peptides may also be synthesized via recombinant techniques well known to those skilled in the art. For example, U.S. Pat. No. 5,595,887, the disclosure of which is herein incorporated by reference, describes methods of forming a variety of relatively small peptides through expression of a recombinant gene construct coding for a fusion protein which includes a binding protein and one or more copies of the desired target peptide. After expression, the fusion protein is isolated and cleaved using chemical and/or enzymatic methods to produce the desired target peptide.

The peptides described in the examples herein were synthesized by a solid phase method. Tables I and II show the amino acid sequences of the peptides described in the experiments reported herein. The following standard single letter code abreviations are used to designate the amino acid residues in the peptides: A-alanine, C-cysteine, D-aspartate, E-glutamate, F-phenylalanine, G-glycine, H-histidine, I-isoleucine, K-lysine, L-leucine, M-methionine, N-asparagine, P-proline, Q-glutamine, R-arginine, S-serine, T-threonine, V-valine, W-tryptophan, Y-tyrosine.

Peptide Carrier Conjugates

The peptides of the present invention may be employed in a monovalent state (i.e., free peptide or a single peptide fragment coupled to a carrier molecule). The peptides may also be employed as conjugates having more than one (same or different) peptide fragment bound to a single carrier molecule. The carrier may be a biological carrier molecule (e.g., a glycosaminoglycan, a proteoglycan, albumin or the like) or a synthetic polymer (e.g., a polyalkyleneglycol or a synthetic chromatography support). Typically, ovalbumin, human serum albumin, other proteins, polyethylene glycol, or the like are employed as the carrier. Such modifications may increase the apparent affinity and/or change the stability of a peptide. The number of peptide fragments associated with or bound to each carrier can vary, but from about 4 to 8 peptide fragments per carrier molecule are typically obtained under standard coupling conditions.

For instance, peptidelcarrier molecule conjugates may be prepared by treating a mixture of peptides and carrier molecules with a coupling agent, such as a carbodiimide. The coupling agent may activate a carboxyl group on either the peptide or the carrier molecule so that the carboxyl group can react with a nucleophile (e.g., an amino or hydroxyl group) on the other member of the peptide/carrier molecule, resulting in the covalent linkage of the peptide and the carrier molecule. Preferably, the conjugate includes at least one peptide fragment which is not linked to the carrier molecule through an amide bond with the α-carboxyl group of the C-terminal aromatic anion acid residue of the LipAr-terminated terminated fragment.

For example, conjugates of a peptide coupled to ovalbumin may be prepared by dissolving equal amounts of lyophilized peptide and ovalbumin in a small volume of water. In a second tube, 1-ethyl-3-(3-dimethylamino-propyl)-carboiimide hydrochloride (EDC; ten times the amount of peptide) is dissolved in a small amount of water. The EDC solution was added to the peptide/ovalbumin mixture and allowed to react for a number of hours. The mixture may then dialyzed (e.g., into phosphate buffered saline) to obtain a purified solution of peptide/ovalbumin conjugate. Peptide/carrier molecule conjugates prepared by this method typically contain about 4 to 5 peptide fragments per ovalbumin molecule.

The invention will be further described by reference to the following detailed examples. The examples are meant to provide illustration and should not be construed as limiting the scope of the present invention.

EXAMPLES

Assay for Inhibition of α4β1 Dependent Cell Adhesion

The assay described below was performed to determine whether specific peptides were capable of inhibiting β1 integrin subunit modulated cell adhesion and, in particular, of inhibiting α4β1 dependent Ramos cell adhesion to IIICS-GST, an α4β1 ligand. IIICS-GST is recombinantly produced fusion protein which contains a fragment from the type III CS region ("IIICS") of plasma fibronectin fused to glutathione-S-transferase ("GST"). The fibronectin fragment corresponds to fibronectin amino acid residues 1961 to 2039 (sequence numbering for fibronectin as designated in U.S. Pat. No. 4,839,464) and includes the DELPQLVTL-PHPNLHGPEILDVPST (SEQ ID NO:46) amino acid sequence ("CS1"; fibronectin residues 1961–1985). A synthetically prepared peptide having the CS1 sequence has been shown to interact with α4β1 integrin on human lymphocytes and promote cell adhesion but does not bind to heparin. In the assay, a 96-well plate was coated with the substrate IIICS-GST. Ramos cells stimulated with the β1 activating monoclonal antibody 8A2 ("Ab 8A2") were pre-incubated with one of the peptides to be evaluated for their ability to adhere to IIICS-GST.

The fusion protein can be constructed by first using PCR primers to amplify the coding sequence for residues 1961–2039 of plama fibronectin. The PCR product can be introduced into a suitable bacterial expression vector in frame with the gene for GST. The resulting vector can be transformed and expressed in a suitable host cell, such as $E$ $Coli$, to produce the fusion protein. If desired, the fusion protein can be purified using a glutathione column. In control experiments in which GST alone was coated onto a 96-well plate, no adhesion of 8A2 activated Ramos cells was observed.

A 96-well plate was coated in triplicate with 50 Tl/well of IIICS-GST diluted to 3–5 Tg/ml in PBS containing 1 mM $CaCl_2$, $MgCl_2$ ("PBS/cations") and incubated overnight at 37° C. The IIICS-GST solution was removed and the wells were blocked with 150 $\mu$/well of PBS/cations containing 0.3% BSA for 1–2 hours at 37° C. During the assay each well contained 100 $\mu$l of Ramos cells (10,000 cells/well) with or without peptide. Ramos cells were washed 3 times in adhesion media (DMEM without phenol red containing 20 mM HEPES and 3 mg/ml BSA). Cells were counted and resuspended at 200,000 cells/ml. Concentrated Ramos cells were labeled for 20 minutes at 37° C. with 50 $\mu$g of the fluorescent label BCECF resuspended in 30 $\mu$l of dimethylsulfoxide ("DMSO"). The labeled cells were centrifuged and resuspended in adhesion media at a concentration of 200,000 cells/ml. The cells were activated with the activating Ab 8A2 at a concentration of 2 $\mu$g/ml purified IgG or 1:1000 culture supernatant.

While the cells were being labeled, inhibiting peptide dilutions were prepared. Lyophilized peptides were weighed and resuspended in adhesion media at a stock concentration of twice the maximal inhibitory concentration. If a peptide was difficult to get into solution, it was initially resuspended in 30 $\mu$l of DMSO. If a peptide needed to be suspended in DMSO, all of the eptides in that particular experiment (including the controls) were suspended in 30 $\mu$l of DMSO. Of the peptides studied in the examples described herein, only the dipeptide "Ile-Tyr" required the use of this technique. The dose-dependent dilutions of peptides were prepared using adhesion media to dilute the stock peptide. Labeled cells were mixed with peptide dilutions for 5 minutes at 37° C. at a final concentration of 100,000 cells/ml and appropriate final peptide concentrations.

The blocking solution was removed from the 96-well plate and the cell/peptide mixture is added at 100 $\mu$l/well (10,000 cells/well) and incubated for 30 minutes at 37° C. An aliquot of standard cells/peptide (100 $\mu$l) was placed at 37° C. for quantitating adhesion. Using aspiration, non-adherent cells were removed from the plate. The standard cells were centrifuged and resuspended in 1000 $\mu$l of adhesion media. The standard cells were added to empty wells at 100, 80, 60, 40, 20 and 0 $\mu$l/well representing 100%, 80%, 60%, 40%, 20% and 0% adhesion, respectively. The plate fluorescence was read at excitation 485 and emission 530. Cell adhesion was represented as percent input cells remaining adherent and was determined by a standard curve of the fluorescence obtained with the standard cells. The experimental fluorescence readings were extrapolated from the standard curve to obtain percent adhesion.

Example 1

Alanine Knockout Analogs of FN-C/H V+Y

Figure 2:
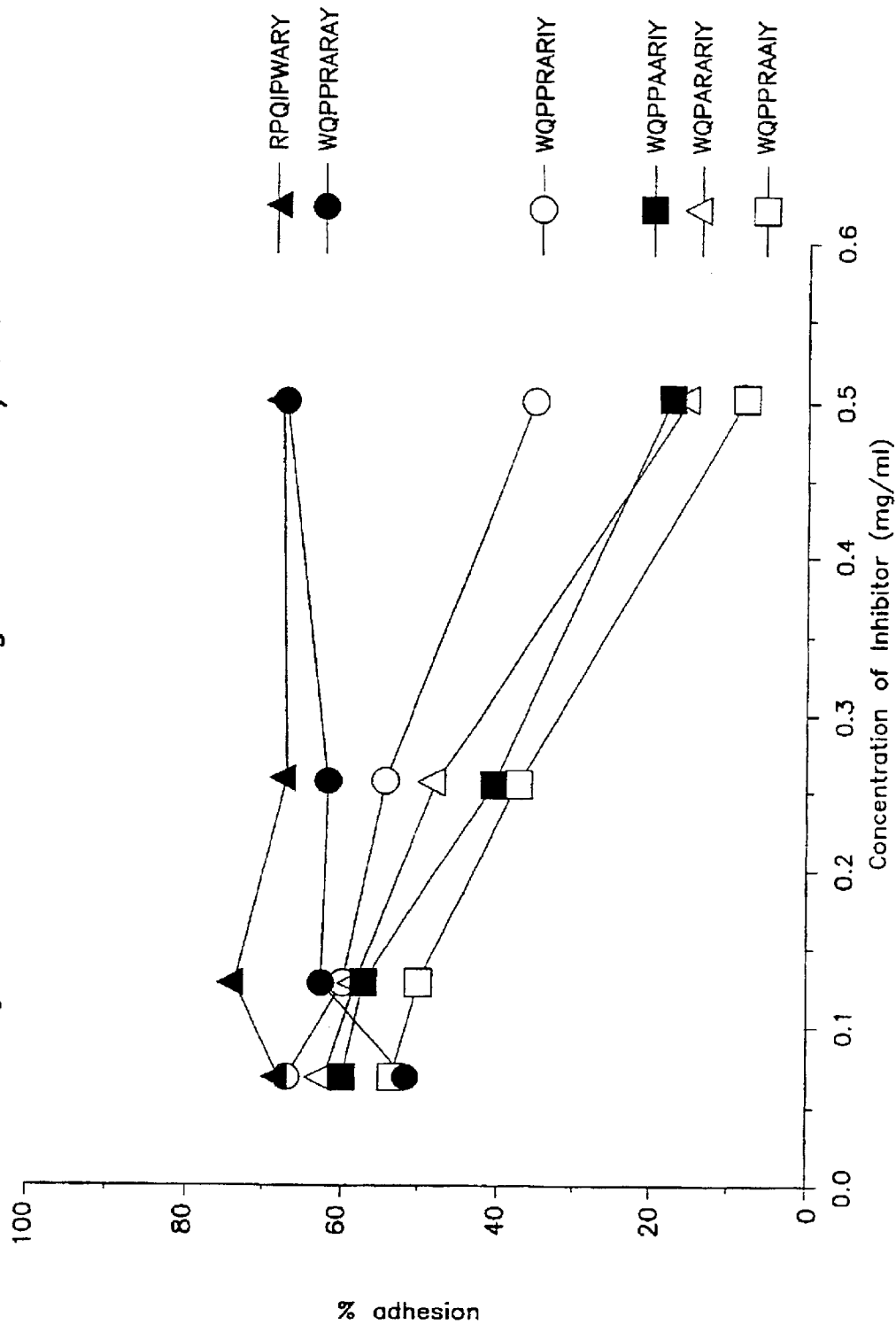
FIG. 2 shows a graph of % adhesion of 8A2 stimulated Ramos cells to IIICS-GST as a function of the concentration of a number of alanine knockout analogs of FN-C/H V+Y. FN C/H V+Y and its scrambled analog sV were included as controls.

To determine which amino acid residues were required for the α4β1 dependent cell adhesion inhibiting activity of FN C/H V+Y, a series of analogs having a single individual residue substituted by alanine were examined. The results are shown in FIGS. 1 and 2. The only alanine substitution which resulted in loss of the ability to inhibit adhesion was substitution of alanine for the isoleucine residue at the penultimate C-terminal position. All of the other alanine knockout peptides showed cell adhesion inhibition comparable to that of FN C/H V+Y. As a control, a scrambled version of the FN C/H V+Y sequence having a C-terminal tyrosine was also examined (RPQIPWARY (SEQ ID NO:2)). The scrambled sequence, which lacked the C-terminal LipAr motif, did not inhibit cell adhesion.

Example 2
C-Terminal Tyrosine Tagged Fibronectin Fragments

Figure 3:
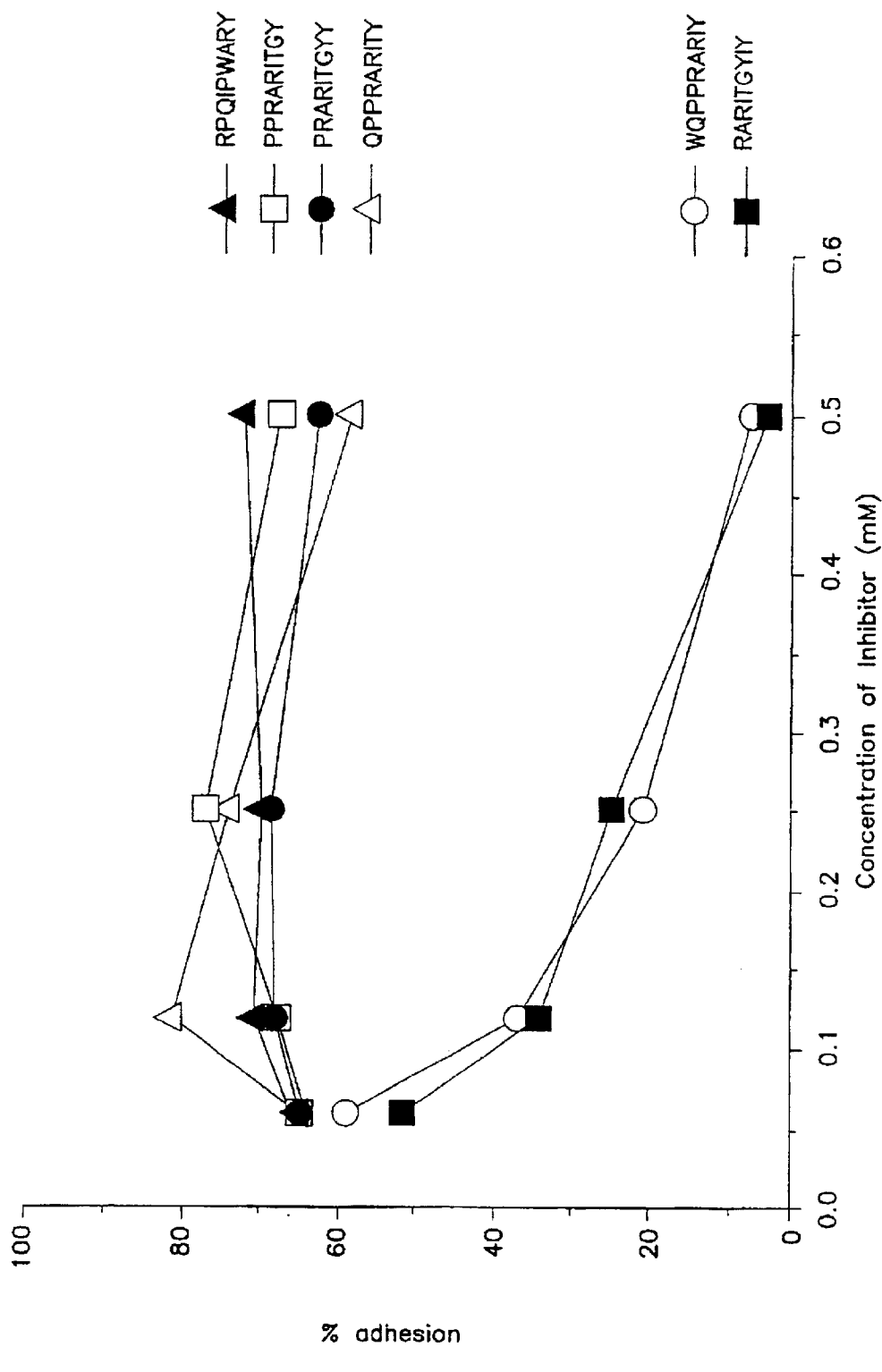
FIG. 3 shows a graph of % adhesion of 8A2 stimulated Ramos cells to IIICS-GST as a function of the concentration of a number of fibronectin fragments tagged with a C-terminal tyrosine residue. FN C/H V+Y and its scrambled analog sV were included as controls.
Figure 4:
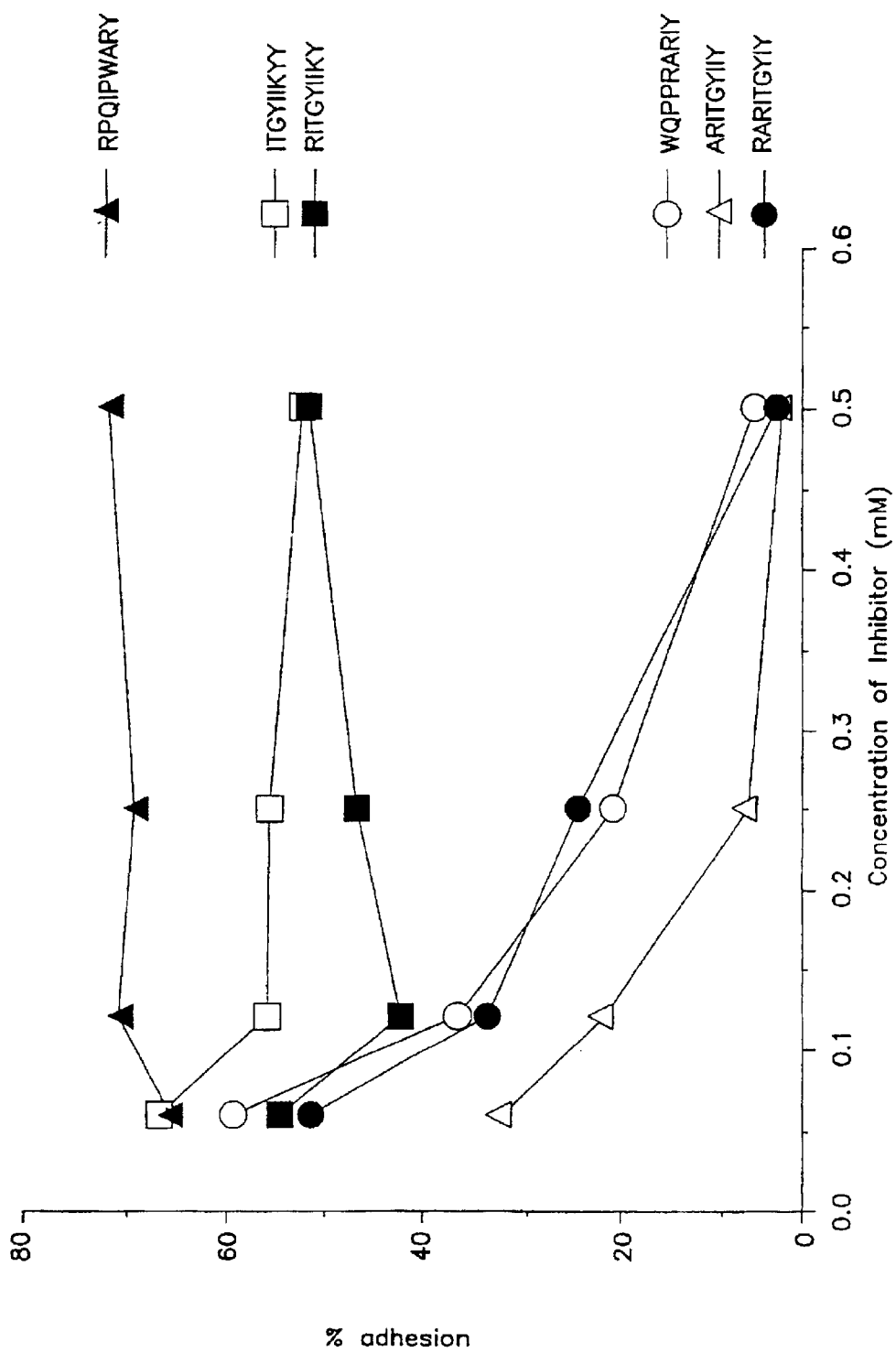
FIG. 4 shows a graph of % adhesion of 8A2 stimulated Ramos cells to IIICS-GST as a function of the concentration of a number of fibronectin fragments tagged with a C-terminal tyrosine residue. FN C/H V+Y and its scrambled analog sV were included as controls.

A number of other C-terminal tyrosine tagged fibronectin fragments were also examined. These peptides corresponded to tyrosine tagged 8 residue fibronectin fragments which were incrementally displaced by one amino acid residue towards the C-terminus of fibronectin (SEQ ID NOs 10–16 in Table I). The results are shown in FIGS. 3 and 4. Unexpectedly, only those peptides which included the C-terminal LipAr motif were active in inhibiting α4β1 integrin dependent cell adhesion. The most active peptide as far as cell inhibiting activity ended with a C-terminal IIY sequence (-Ile-Ile-Tyr-). The full sequence of this peptide was ARITGYIIY (SEQ ID NO:14). The sequences of the other two Y-tagged fibronectin fragments which exhibited α4β1 integrin dependent cell adhesion inhibition was RARITGYIY (SEQ ID NO:13). The Y-tagged fibronectin fragments with a C-terminal Thr-Tyr ("TY"), Gly-Tyr ("GY"), Tyr-Tyr ("YY") or Lys-Tyr ("KY") motif did not inhibit α4β1 integrin dependent adhesion of the Ramos cells.

Example 3
Scrambled IY Tagged Sequences

Figure 5:
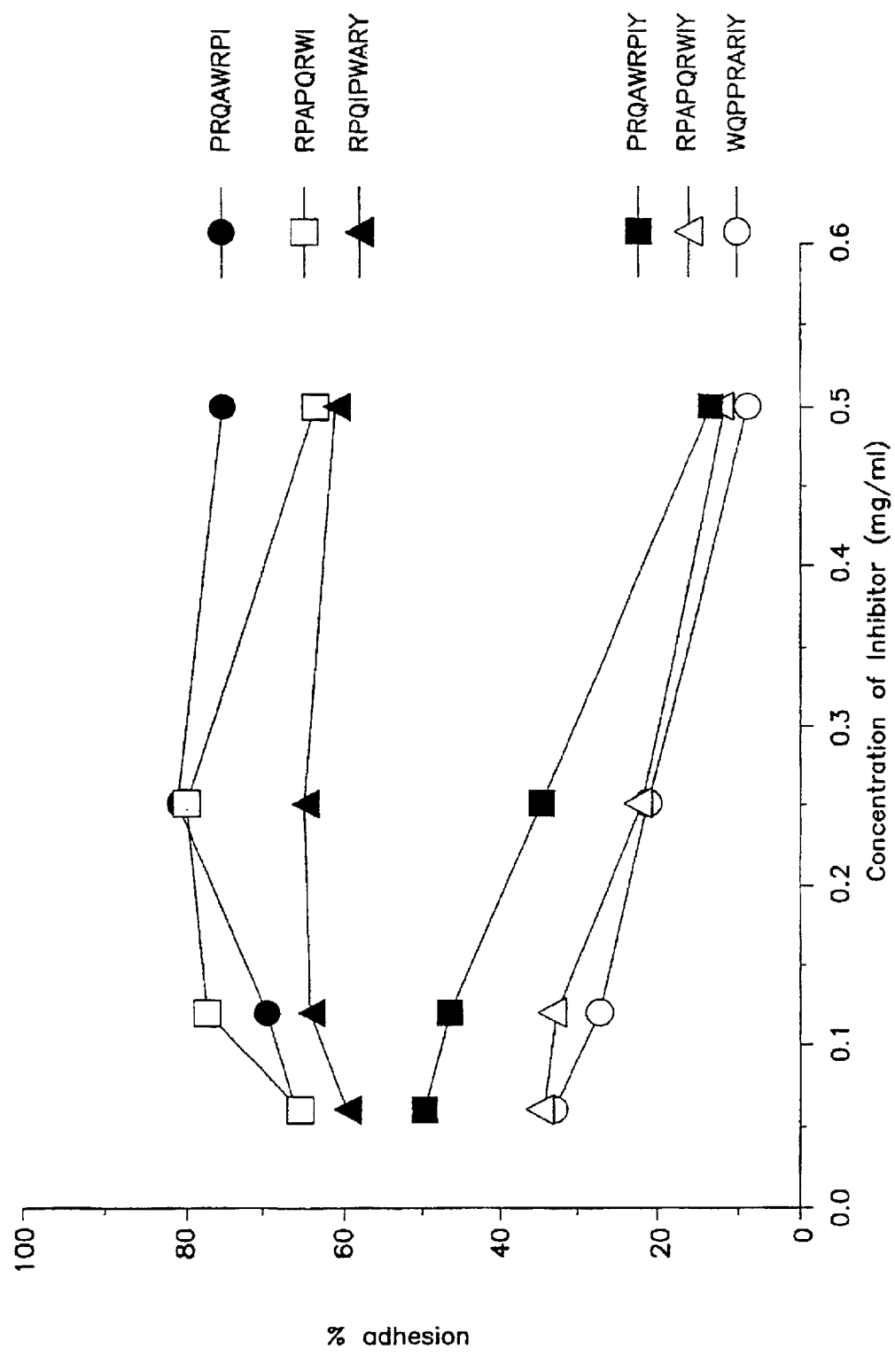
FIG. 5 shows a graph of % adhesion of 8A2 stimulated Ramos cells to IIICS-GST as a function of the concentration of two "IY" C-terminated peptides and their corresponding "des-Y" analogs. FN C/H V+Y and its scrambled analog sV were included as controls.
Figure 6:
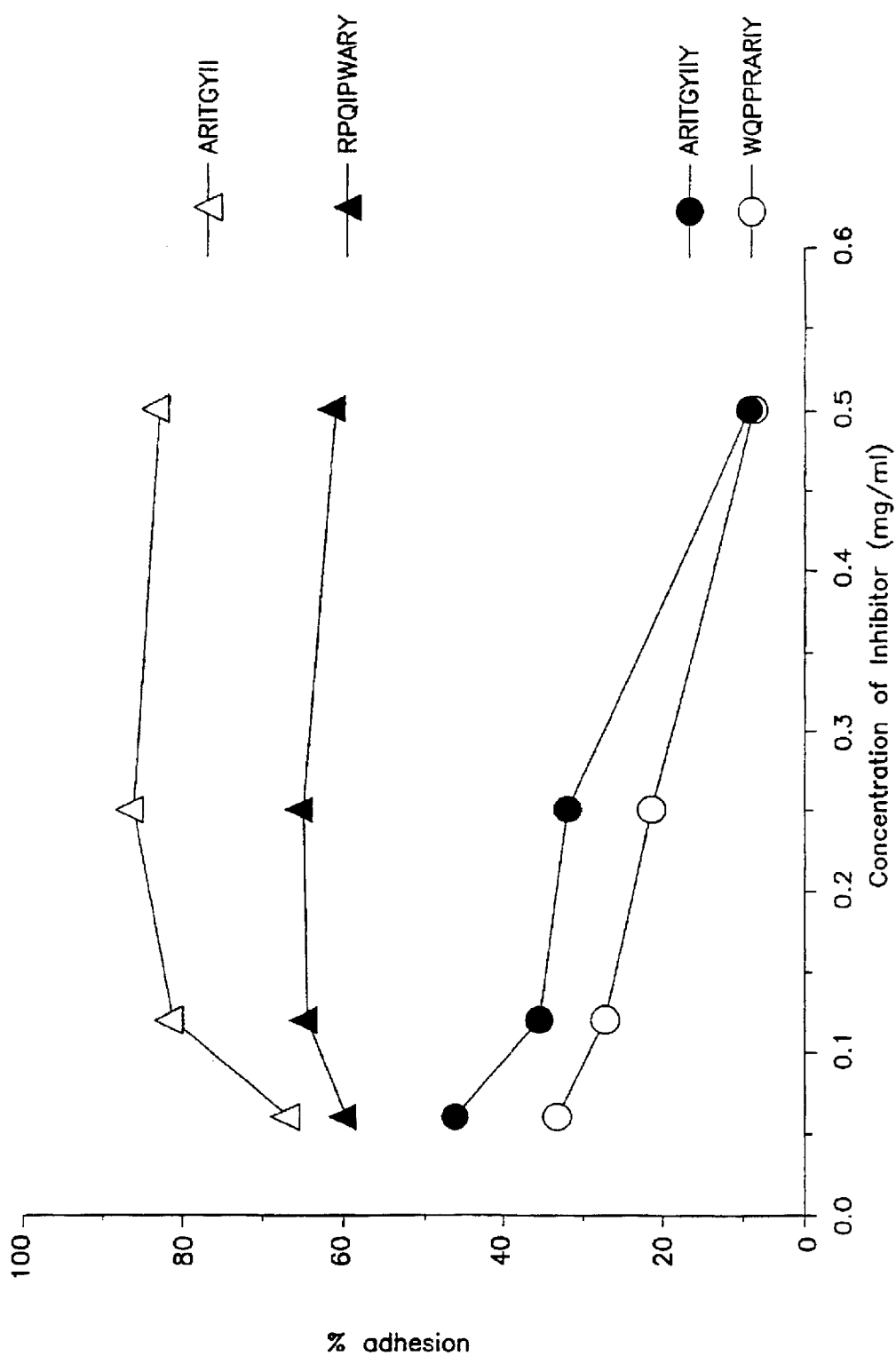
FIG. 6 shows a graph of % adhesion of 8A2 stimulated Ramos cells to IIICS-GST as a function of the concentration of another "IY" C-terminated peptide and its corresponding "des-Y" analogs. FN C/H V+Y and its scrambled analog sV were included as controls.

To examine the effect of the N-terminal seven amino acid sequence on inhibition of α4β1 dependent cell adhesion, three Ile-Tyr C-terminated scrambled versions of FN C/H V+Y were examined. The activity of the eight amino acid des-tyrosine analogs of the two scrambled peptides were also examined as controls. The results shown in FIGS. 5 and 6 clearly demonstrate that only the "LipAr" C-terminated peptides ARITGYIIY (SEQ ID NO:14), PRQAWRPIY (SEQ ID NO:18) and RPAPQRWIY (SEQ ID NO:20) inhibited cell adhesion. In each instance, the identical primary amino acid sequence lacking the C-terminal tyrosine residue did not inhibit Ramos cell adhesion. Although not conclusive, this result strongly suggests that there is little or no requirement for the N-terminal portion of the sequence in order for a peptide with a C-terminal LipAr motif to inhibit β1 integrin subunit dependent cell adhesion.

Example 4
Inhibition by Short IY Terminated Peptides

Figure 7:
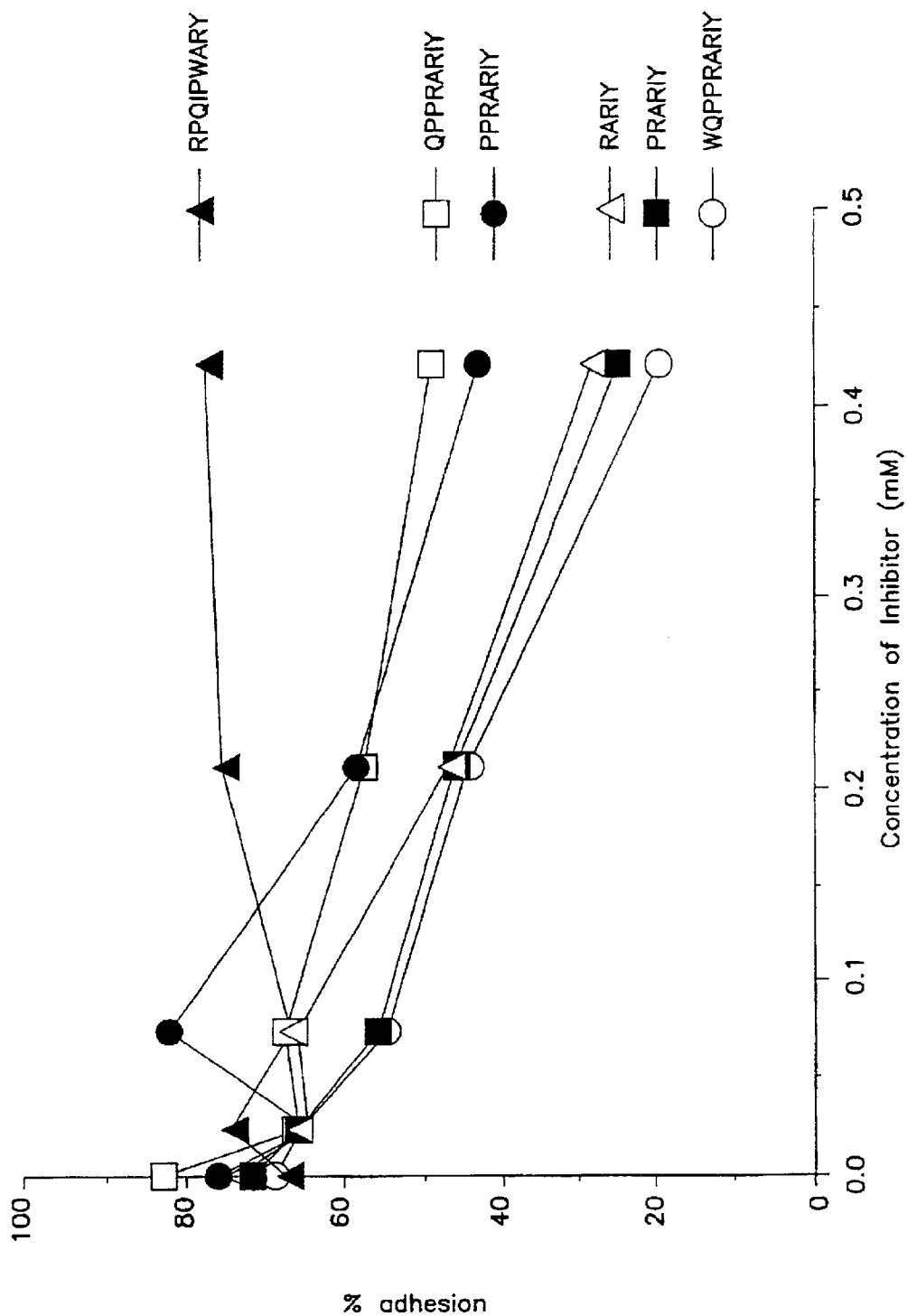
FIG. 7 shows a graph of % adhesion of 8A2 stimulated Ramos cells to IIICS-GST as a function of the concentration of a number of truncated analogs of FN C/H V+Y. Controls included FN C/H V+Y and its scrambled analog sV.
Figure 8:
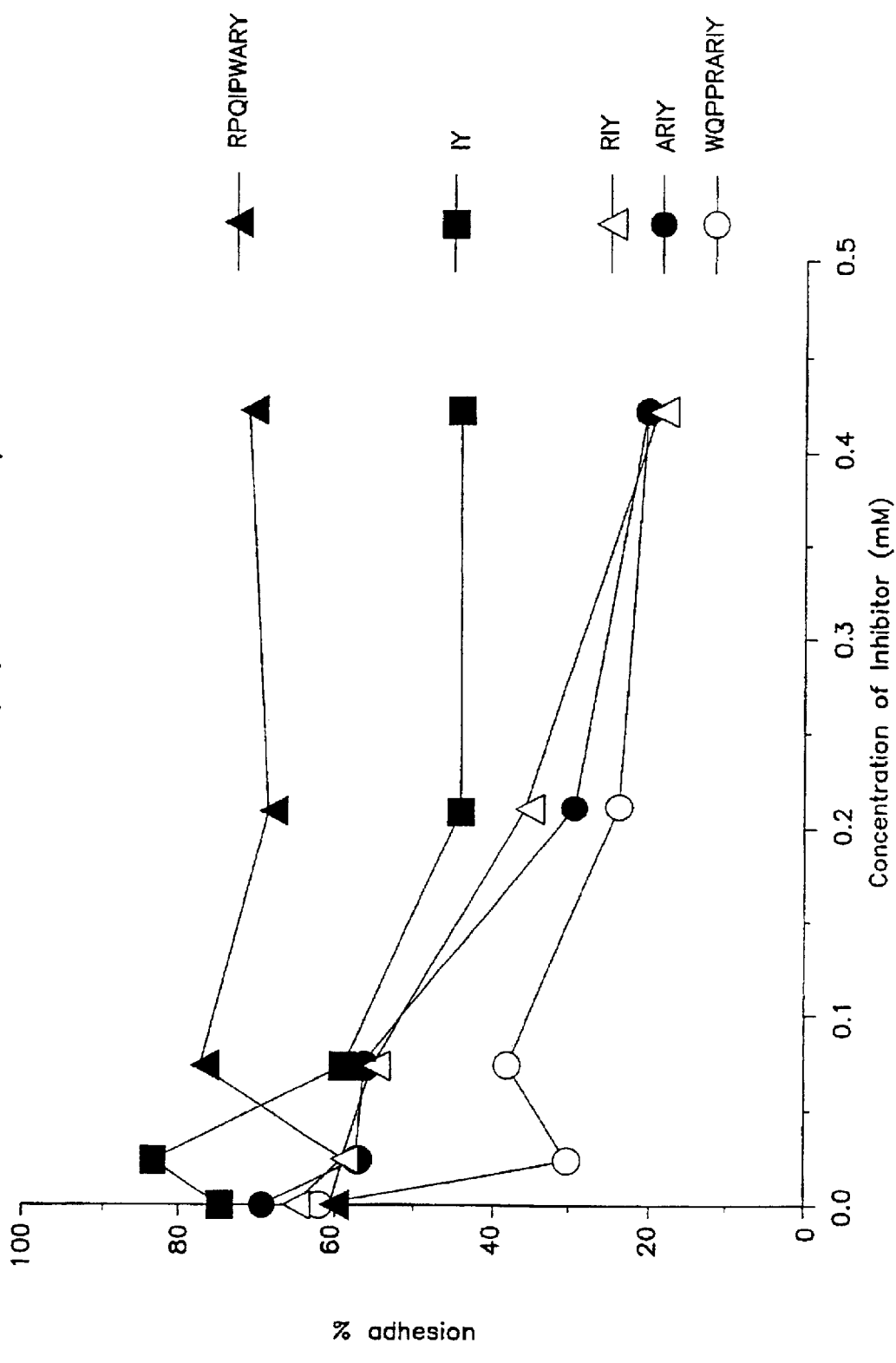
FIG. 8 shows a graph of % adhesion of 8A2 stimulated Ramos cells to IIICS-GST as a function of the concentration of a number of truncated analogs of FN C/H V+Y. FN C/H V+Y and its scrambled analog sV were employed as controls.

To establish the minimum size of IY-peptide required for inhibition of α4β1 dependent cell adhesion, a study was carried out on a series of truncated FN C/H V+Y analogs in which the N-terminal residue was systematically deleted. The results are shown in FIGS. 7 and 8. The data establish that the "IY" dipeptide itself is capable of inhibiting α4β1 integrin dependent cell adhesion. The activity of the dipeptide was less than that observed with a number of longer IY terminated peptides. The cell adhesion inhibiting activity of a 6 residue peptide, PRARIY (SEQ ID NO:24), and a 5 residue peptide, RARIY (SEQ ID NO:25), was comparable on an equimolar basis to that of the 9 residue peptide, Y-tagged FN C/H V. These two shortened peptides both contain two arginine residues ("R") and having a net charge of +2 at neutral pH. Other short IY-terminated peptides with the sequences QPPRARIY (SEQ ID NO:22), PPRARIY (SEQ ID NO:23), ARIY (SEQ ID NO:26) and RIY also exhibited α4β1 integrin dependent cell adhesion inhibition activity. The cell adhesion inhibition activity of ARIY (SEQ ID NO:26) and RIY was comparable on an equimolar basis to that of Y-tagged FN C/H V.

Example 5
Inhibition of Ile-Tyr versus Ile and/or Tyr

Figure 9:
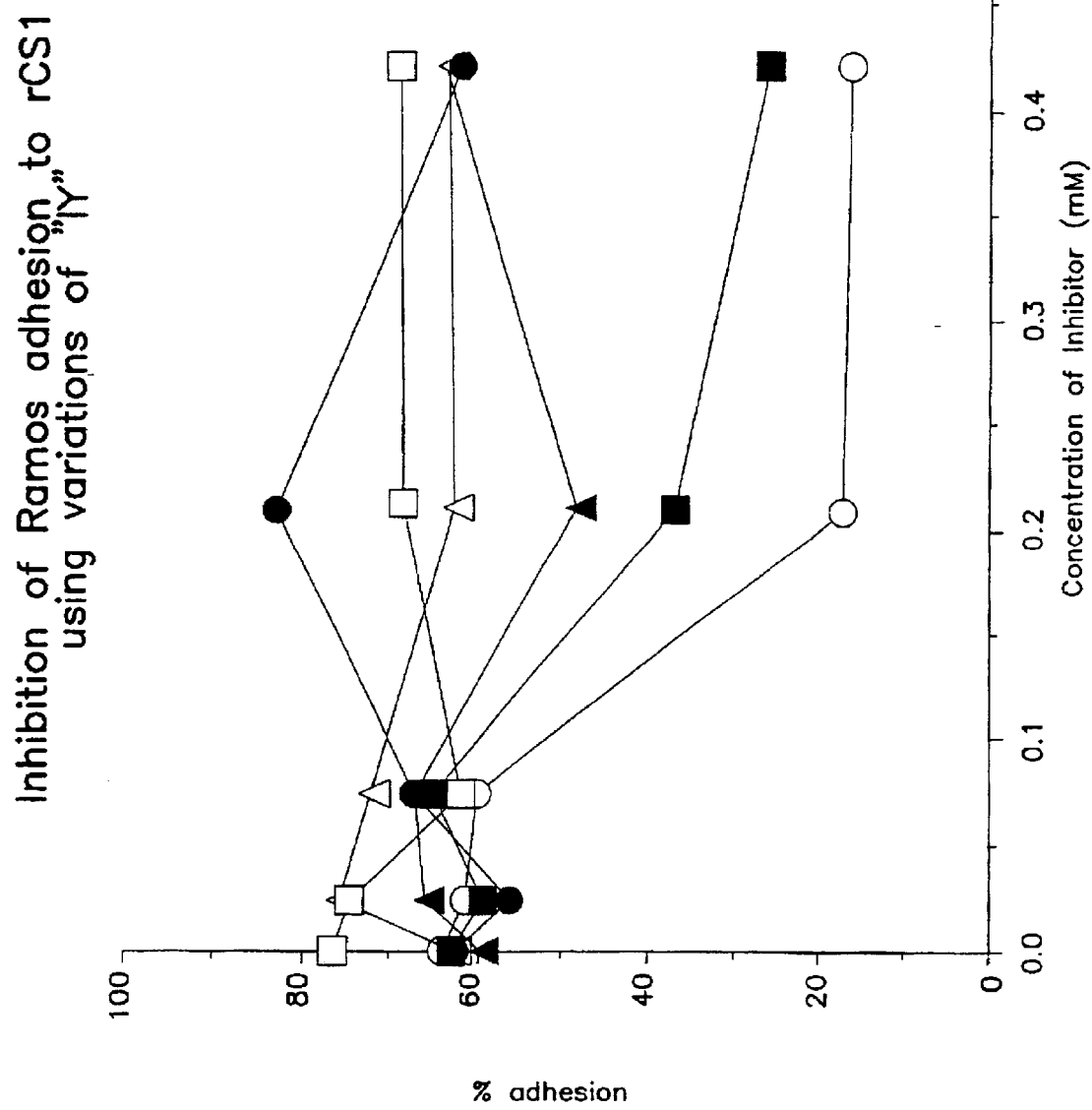
FIG. 9 shows a graph of % adhesion of 8A2 stimulated Ramos cells to IIICS-GST as a function of the concentration of "IY" and its component single amino acid residues. FN C/H V+Y and its scrambled analog sV were employed as controls.

As a control experiment, the activity of the single amino acids, isoleucine and tyrosine, alone and as part of a mixture, was also examined in the cell adhesion inhibition activity. The results shown in FIG. 9 establish that even a mixture of the individual amino acids isoleucine and tyrosine is insufficient to inhibit cell adhesion at anything close to the concentration where the dipeptide "Ile-Tyr" is active.

Example 6
Inhibition by "Xaa-Tyr" Terminated Peptides

Figure 10:
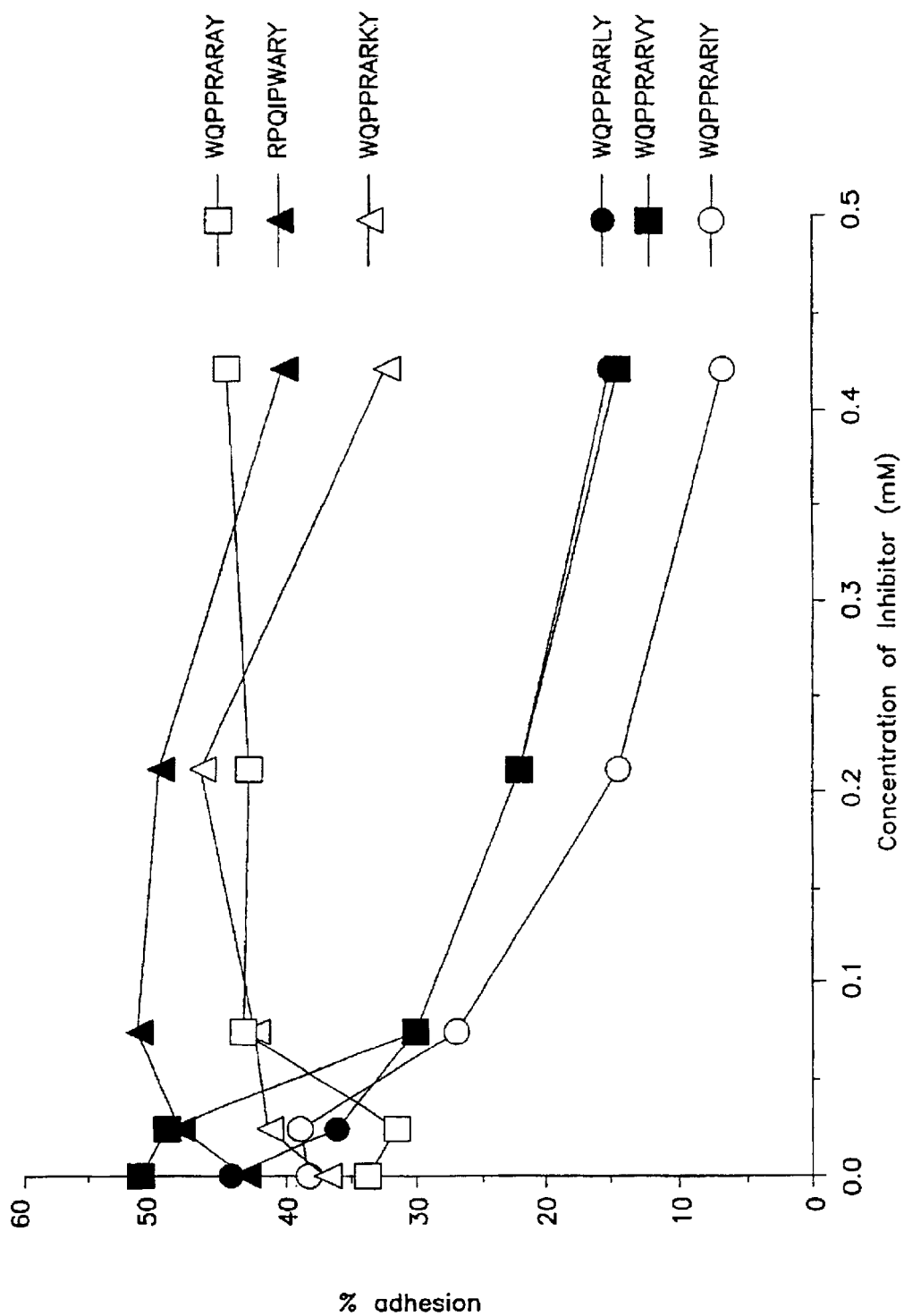
FIG. 10 shows a graph of % adhesion of 8A2 stimulated Ramos cells to IIICS-GST as a function of the concentration of a several C-terminal penultimate substitution variants of FN C/H V+Y. FN C/H V+Y and its scrambled analog sV were employed as controls.
Figure 11:
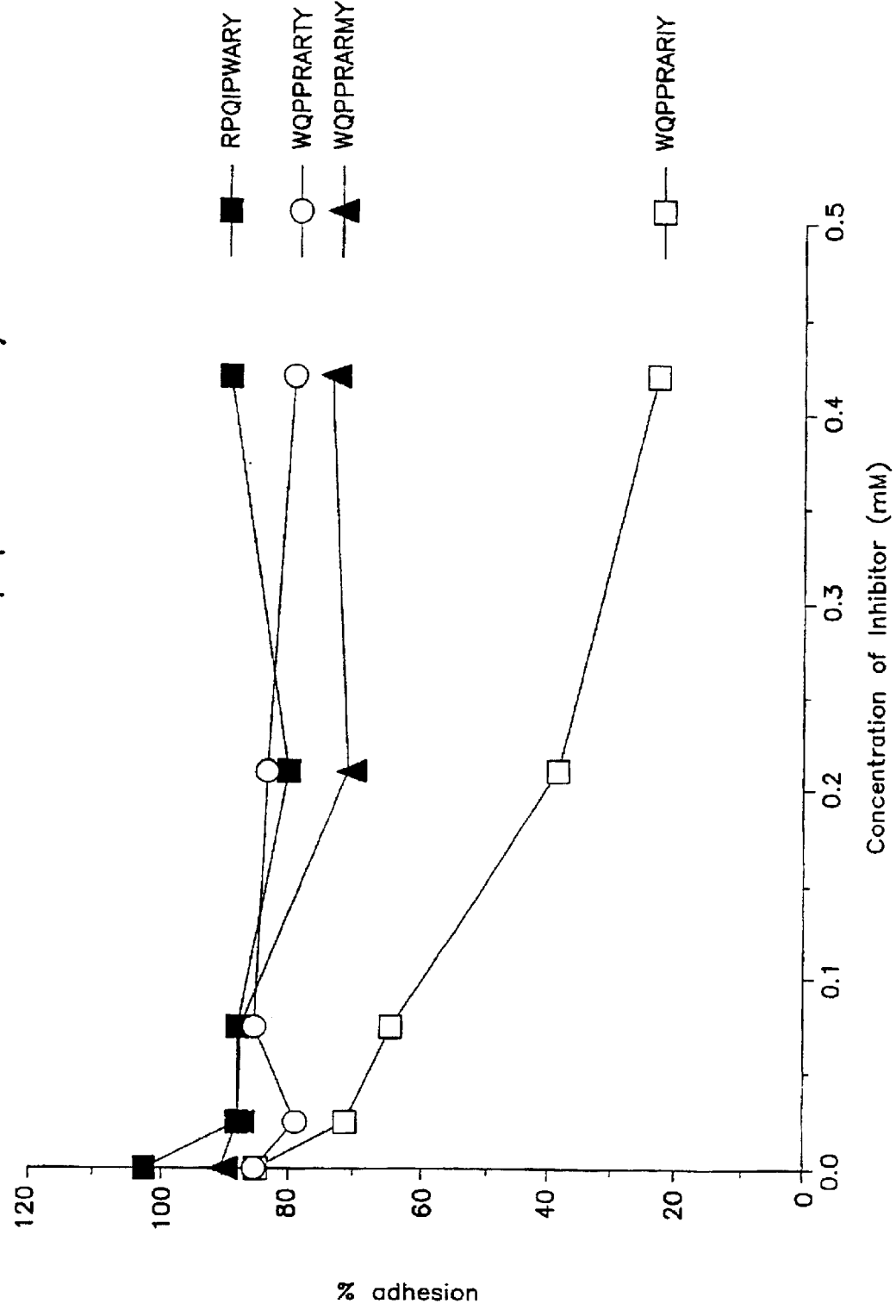
FIG. 11 shows a graph of % adhesion of 8A2 stimulated Ramos cells to IIICS-GST as a function of the concentration of a several C-terminal penultimate substitution variants of FN C/H V+Y. FN C/H V+Y and its scrambled analog sV were employed as controls.

To examine the structural requirements of the "LipAr" motif, the inhibition of α4β1 dependent Ramos cell adhesion was examined for a number of FN C/H V+Y analogs with substitutions at the penultimate C-terminal amino acid residue. The results are shown in FIGS. 10 and 11. The two analogs with a lipophilic aliphatic side chain residue (Leu or Val) substituted at the penultimate C-terminal position, WQPPRARLY (SEQ ID NO:29) and WQPPRARVY (SEQ ID NO:29), had cell adhesion inhibiting activity comparable to that of FN C/H V+Y. The corresponding analogs with a basic residue (Lys), a hydroxy side chain residue (thr), a methionine residue (Met) or an alanine residue (Ala) in penultimate C-terminal position were substantially inactive in the assay.

Example 7
Inhibition by C-Terminal Variants

Figure 12:
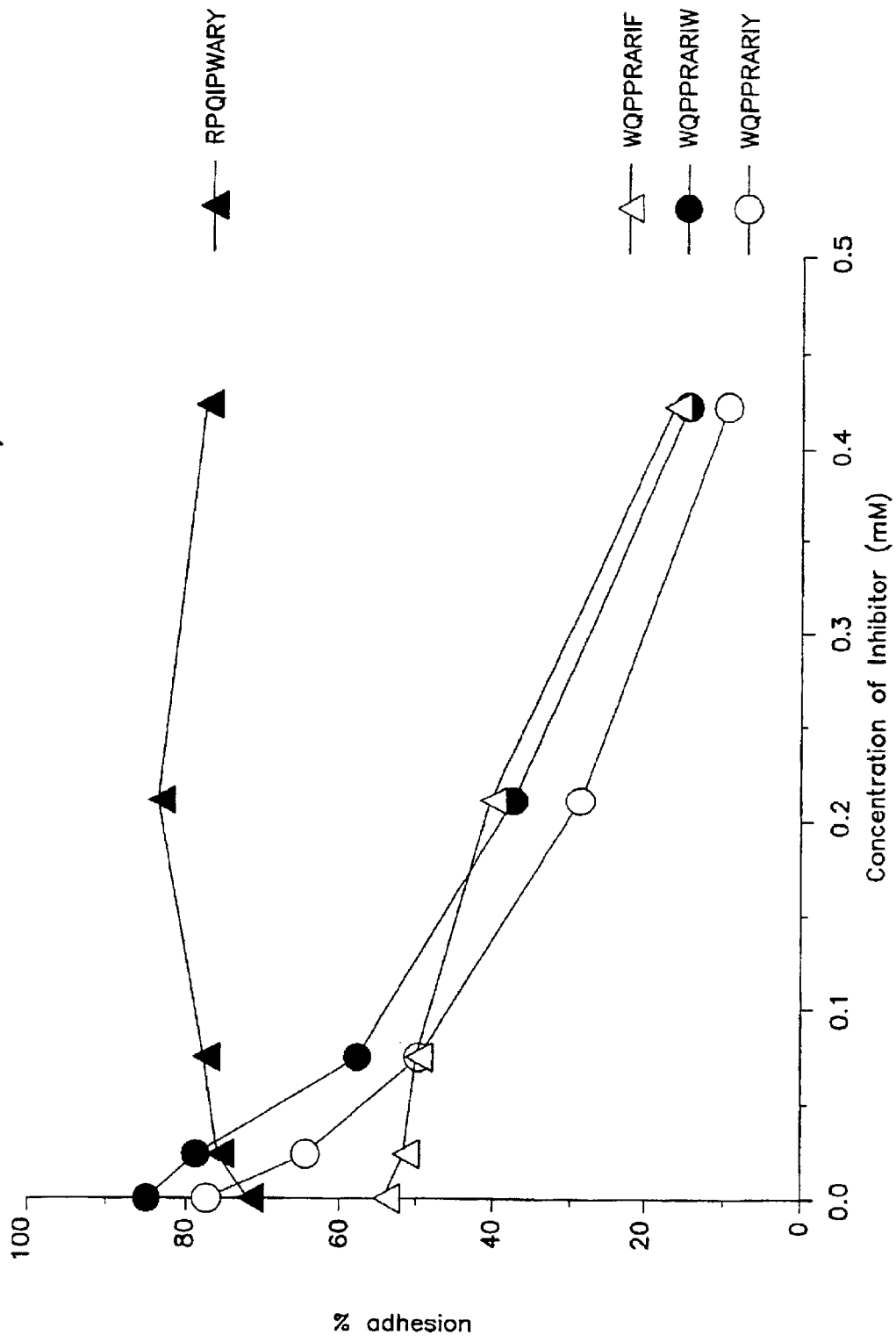
FIG. 12 shows a graph of % adhesion of 8A2 stimulated Ramos cells to IIICS-GST as a function of the concentration of a several C-terminal substitution variants of FN C/H V+Y. FN C/H V+Y and its scrambled analog sV were employed as controls.

To examine the structural requirements of the "LipAr" motif, the inhibition of α4β1 dependent Ramos cell adhesion was examined for a number of FN C/H V+Y analogs with substitutions at the C-terminal amino acid residue. The results are shown in FIG. 12. The two analogs with a C-terminal amino acid residue having a side chain which includes an aromatic group (Phe or Trp) at the C-terminal position, WQPPRARIF (SEQ ID NO:32) and WQPPRARIW (SEQ ID NO:33), had cell adhesion inhibiting activity comparable to that of FN C/H V+Y.

Example 8
Inhibition by C-Terminal Variants

Figure 13:
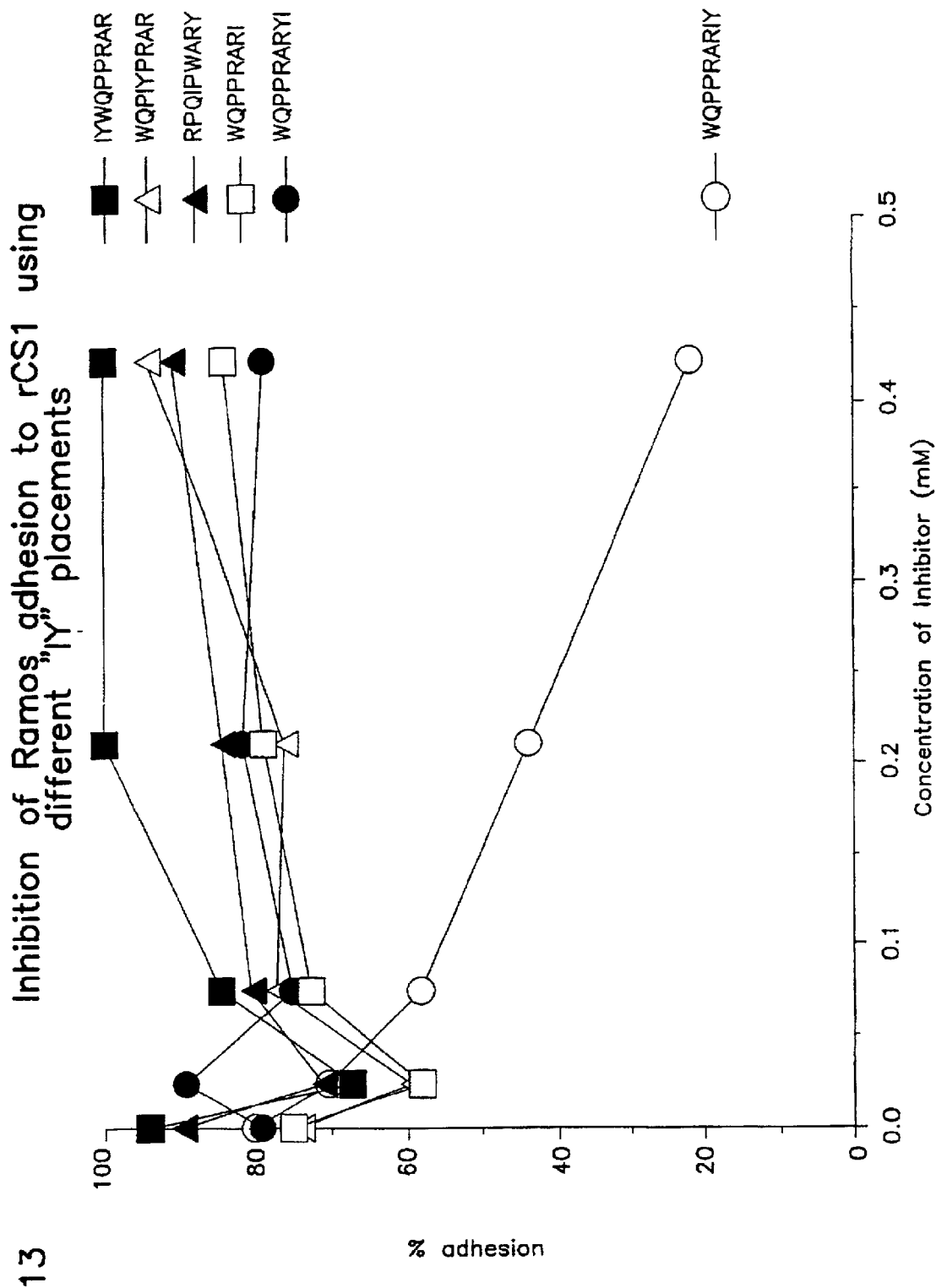
FIG. 13 shows a graph of % adhesion of 8A2 stimulated Ramos cells to IIICS-GST as a function of the concentration of "TY" positional variants of FN C/H V+Y. FN C/H V+Y, its scrambled analog sV, and untagged FN C/H V (WQPPRARI (SEQ ID NO: 37)) were employed as controls.

The inhibition of α4β1 dependent Ramos cell adhesion for a number of FN C/H V+Y analogs with differently positioned IY motifs was examined. The results are shown in FIG. 13. Peptides with the "IY" motif at the N-terminus, IYWQPPRAR (SEQ ID NO:34), or in the middle of the peptide, WQPIYPRAR (SEQ ID NO:35) were inactive in the assay. Switching the order of the Ile and Tyr residues at the C-terminus of an FN C/H V+Y analog, WQPPRARYI (SEQ ID NO:36), also resulted in a peptide which was inactive in the α4β1 dependent Ramos cell adhesion inhibition assay. Finally, control peptide having the tyrosine tag removed from the C-terminus of FN C/H V+Y, WQPPRARI (SEQ ID NO:35), was. also inactive in the assay.

Example 9
Inhibition of Adhesion by a Negatively Charged "LipAr" Peptide

Figure 14:
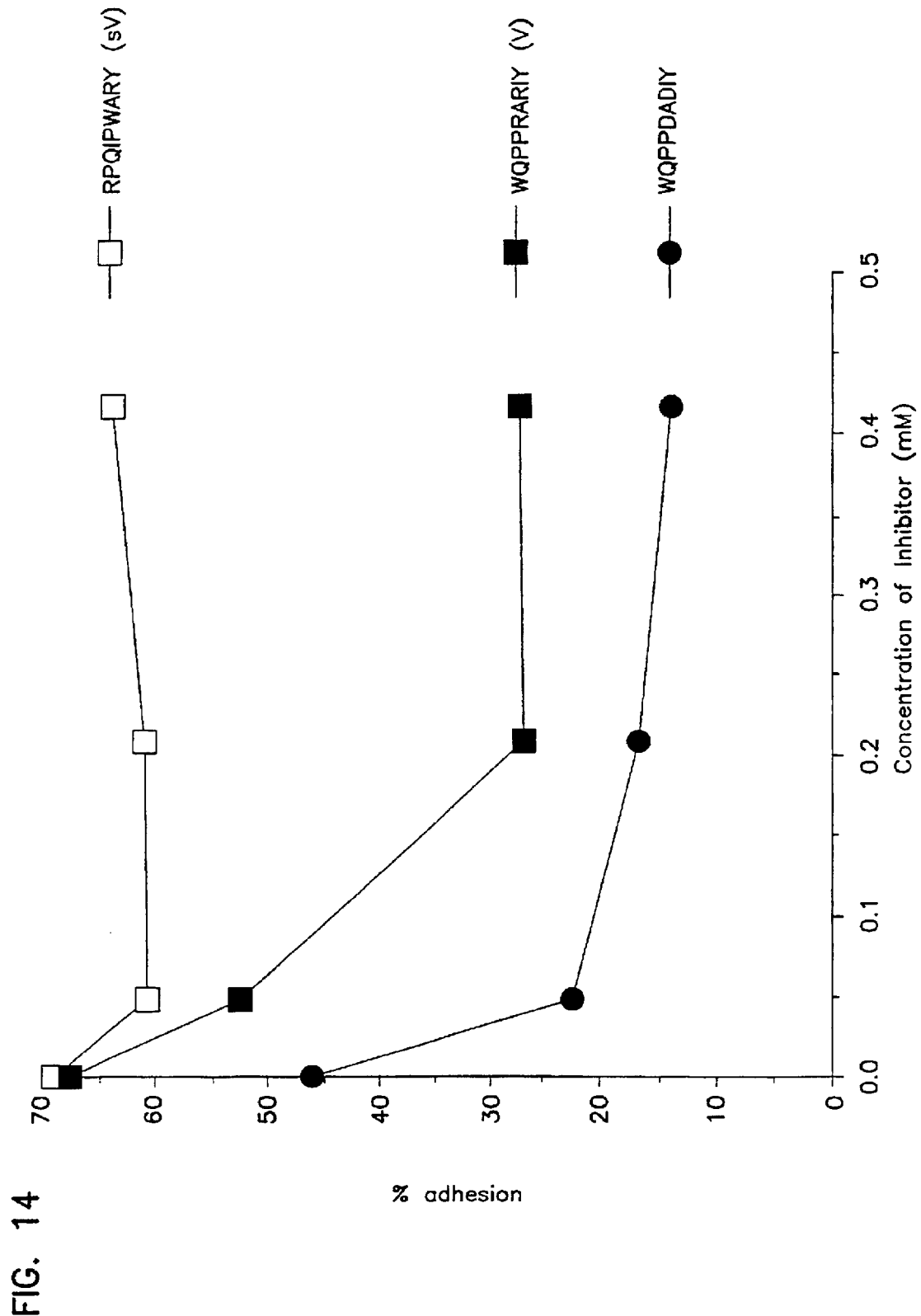
FIG. 14 shows a graph of % adhesion of 8A2 stimulated Ramos cells to IIICS-GST as a function of the concentration of a negatively charged LipAr terminated peptide. FN C/H V+Y and its scrambled analog sV were employed as controls.

All the the LipAr terminated peptides described in the above examples which were active in the Ramos cell adhesion inhibition assay have a net positive charge. In order to determine whether a net positive charge is required for this activity, an FN-C/H V+Y analog in which the 2 arginines (positively charged) were replaced by aspartic acid residues (negatively charged) was evaluated. Importantly, the C-terminal "LipAr" motif ("IY") was retained in this peptide, WQPPPDADIY (SEQ ID NO:38). FIG. 14 clearly demonstrates that substitution of the arginines with aspartic acid residues does not alter the ability of the peptide to inhibit β1 integrin subunit dependent adhesion, thereby further demonstrating the importance of the "LipAr" motif to this activity.

Example 10
Inhibition of adhesion by PRARIY versus PRARI

Figure 15:
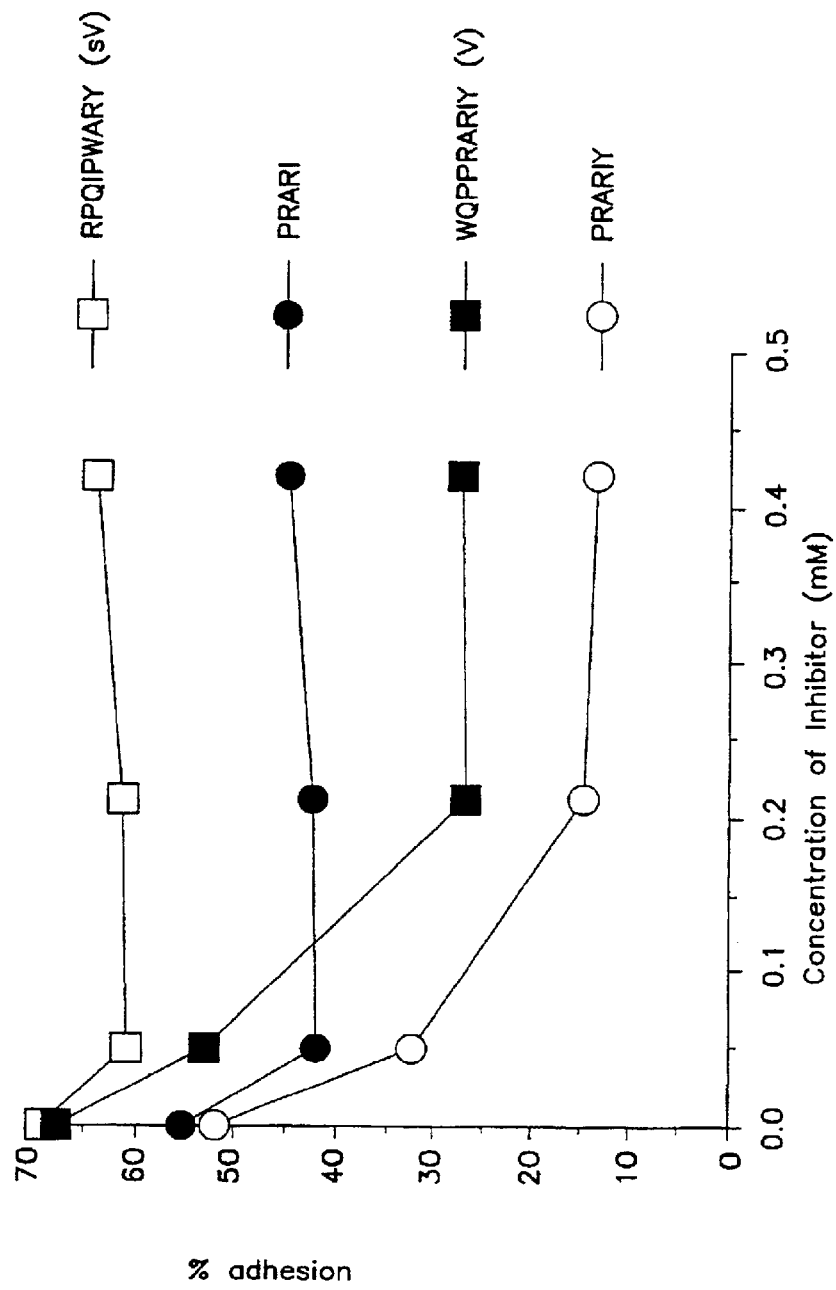
FIG. 15 shows a graph of % adhesion of 8A2 stimulated Ramos cells to IIICS-GST as a function of the concentration of PRARIY (SEQ ID NO: 24) and PRARI (SEQ ID NO: 39). FN C/H V+Y and its scrambled analog sV were employed as controls.

In an experiment which further demonstrated the correlation of a C-terminal LipAr motif with β1 integrin subunit dependent adhesion adhesion, the peptide PRARIY (SEQ ID NO:24) and the corresponding sequence lacking the terminal aromatic residue ("Tyr") were evaluated for their ability to inhibit adhesion in the Ramos cell assay. Consistent with the previous results demonstrating the requirement for a C-terminal "LipAr" motif, PRARIY but not PRARI was able to inhibit α4β1 mediated Ramos cell adhesion to IIICS-GST (see FIG. 15).

Example 11
Inhibition of α5β1 Integrin Dependent Adhesion

Figure 16:
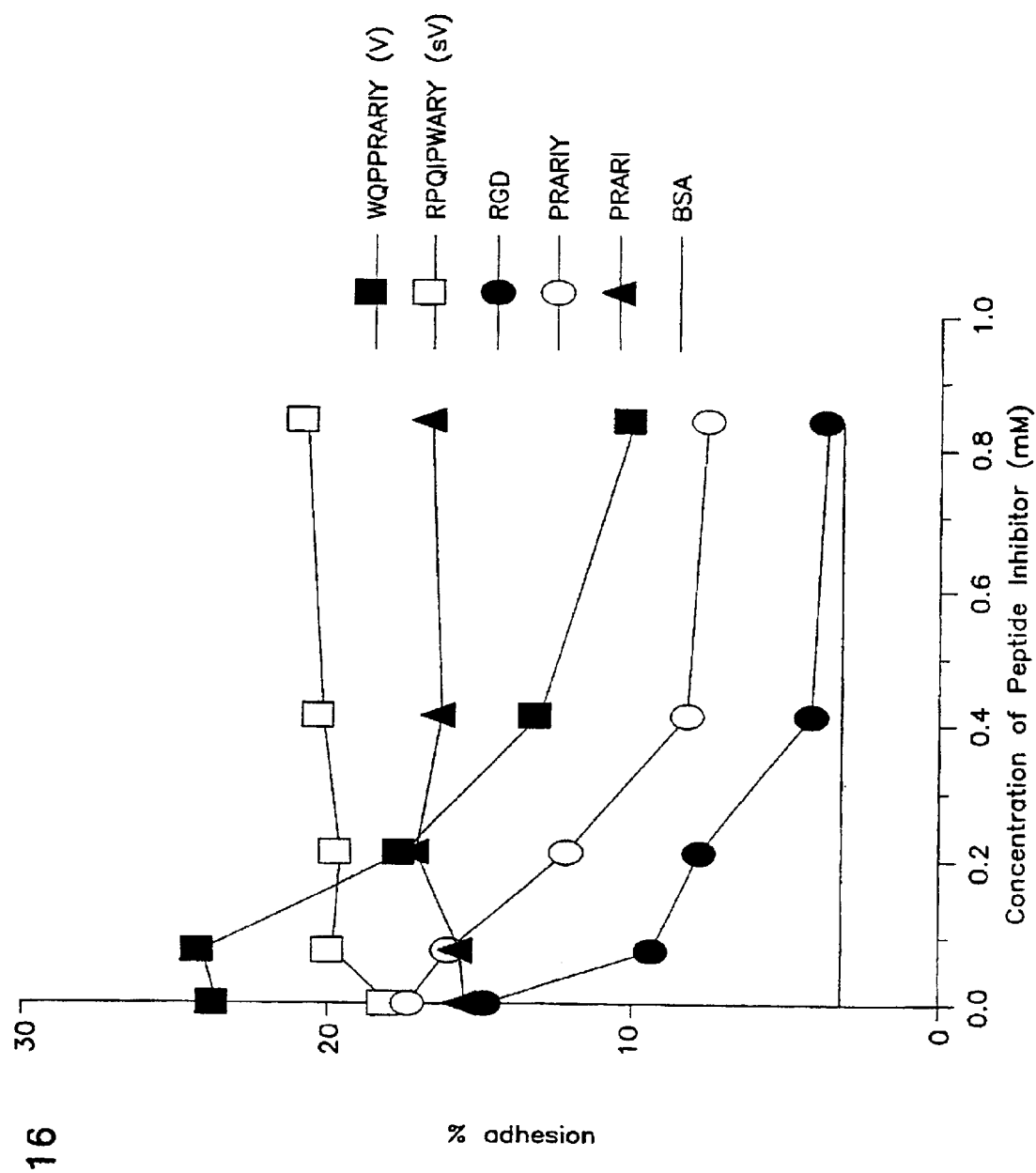
FIG. 16 shows a graph of % adhesion of the α5β1 integrin dependent $Mn^{+2}$ stimulated adhesion of erythroleukemic K562 cells to fibronectin ("FN") as a function of the concentration of PRARIY (SEQ ID NO: 24) and PRARI (SEQ ID NO: 39). FN C/H V+Y, its scrambled analog sV, RGD and BSA (bovine serun albumin) were employed as controls.
Figure 17:
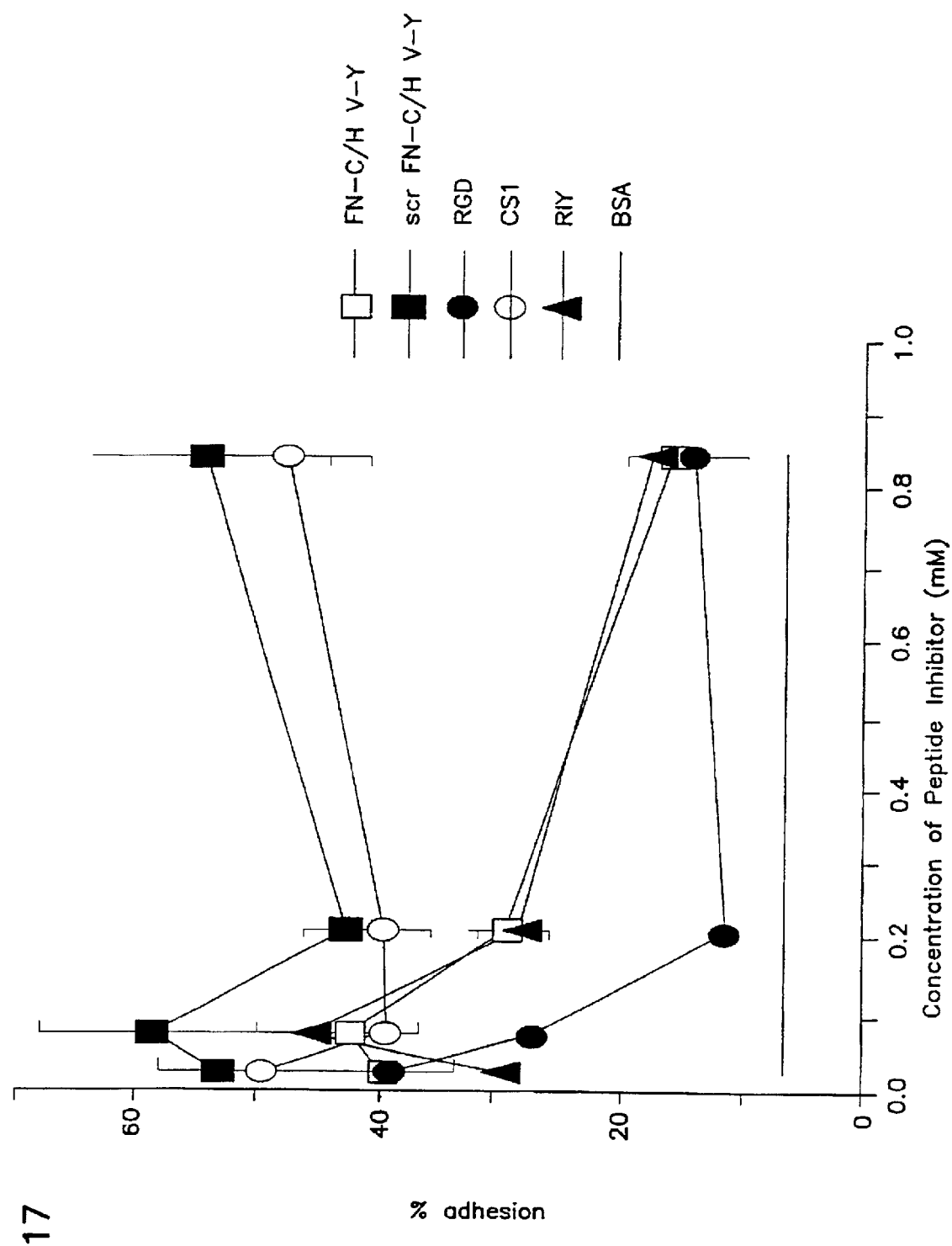
FIG. 17 shows a graph of % adhesion of the α5β1 integrin dependent $Mn^{+2}$ stimulated adhesion of erythroleukernic K562 cells to fibronectin ("FN") as a function of the concentration of RIY. FN C/H V+Y, its scrambled analog sV, RGD, CS1 and BSA (bovine serum albumin) were employed as controls.

To determine whether inhibition of adhesion by C-terminal isoleucine-tyrosine is restricted to α4β1 integrin adhesion, peptide RIY and peptides ending in isoleucine-tyrosine (PRARIY) and isoleucine (PRARI) were evaluated for the ability to inhibit α5β1 integrin-mediated cell adhesion. The cell adhesion assay was carried out as described above. K562 cells stimulated with 1 mM $MnCl_2$ were preincubated with the indicated concentration of peptide and allowed to adhere to FN. The results are shown in FIGS. 16 and 17, where (V), (SV) represent peptides FN-C/H V–Y and scrambled FN-C/H V–Y, respectively. Each data point represents the mean of triplicate determinations and the error bars represent the standard deviation of the mean. The solid black line represents adhesion to the negative control substrate, BSA.

Adhesion of the erythroleukemic cell line K562, which expresses α5β1 but not α4β1 integrin, to FN is completely inhibited following preincubation with soluble RGD or FN-C/H V–Y at the maximal concentration tested, 0.84 mM (FIGS. 16, 17). The half-maximal inhibitory concentration for soluble peptides RGD and FN-C/H V–Y was 0.1 mM and 0.2 mM, respectively. Furthermore, addition to peptides RIY or PRARIY, but not PRARI, completely inhibited α5β1 dependent K562 adhesion to FN with at the maximal concentration tested, 0.84 mM. The half-maximal inhibitory concentration of both RIY and PRARIY was approximately 0.2 mM, similar to that observed for RGD and FN-C/H V–Y. These results demonstrate that, like peptide FN-CIH V–Y, the smallest, maximally active peptide RIY and peptides ending in isoleucine-tyrosine, but not isoleucine (PRARI), inhibit α5β1 (in addition to α4β1) integrin-mediated adhesion (see FIGS. 16 and 17).

Example 12
Inhibition of α2β1, α3β1 Integrin Dependent Adhesion

An experiment was conducted to examine the ability of FN-C/H V+Y (SEQ ID NO:1) to inhibit α2β1, α3β1 integrin dependent cell adhesion using an assay based on human melanoma cells (M14#5).

Laminin, type IV collagen and BSA were coated overnight in a 96 well microtiter plate at 10 μg/ml and blocked with 0.3% BSA. M14#5 cells were preincubated with 0.5 mg/ml of peptide (equivalent to 0.42 mM FN-C/H V and scrambled FN-C/H V and 0.17 mM CSI) and allowed to adhere to substrates for 30 minutes.

Figure 18:
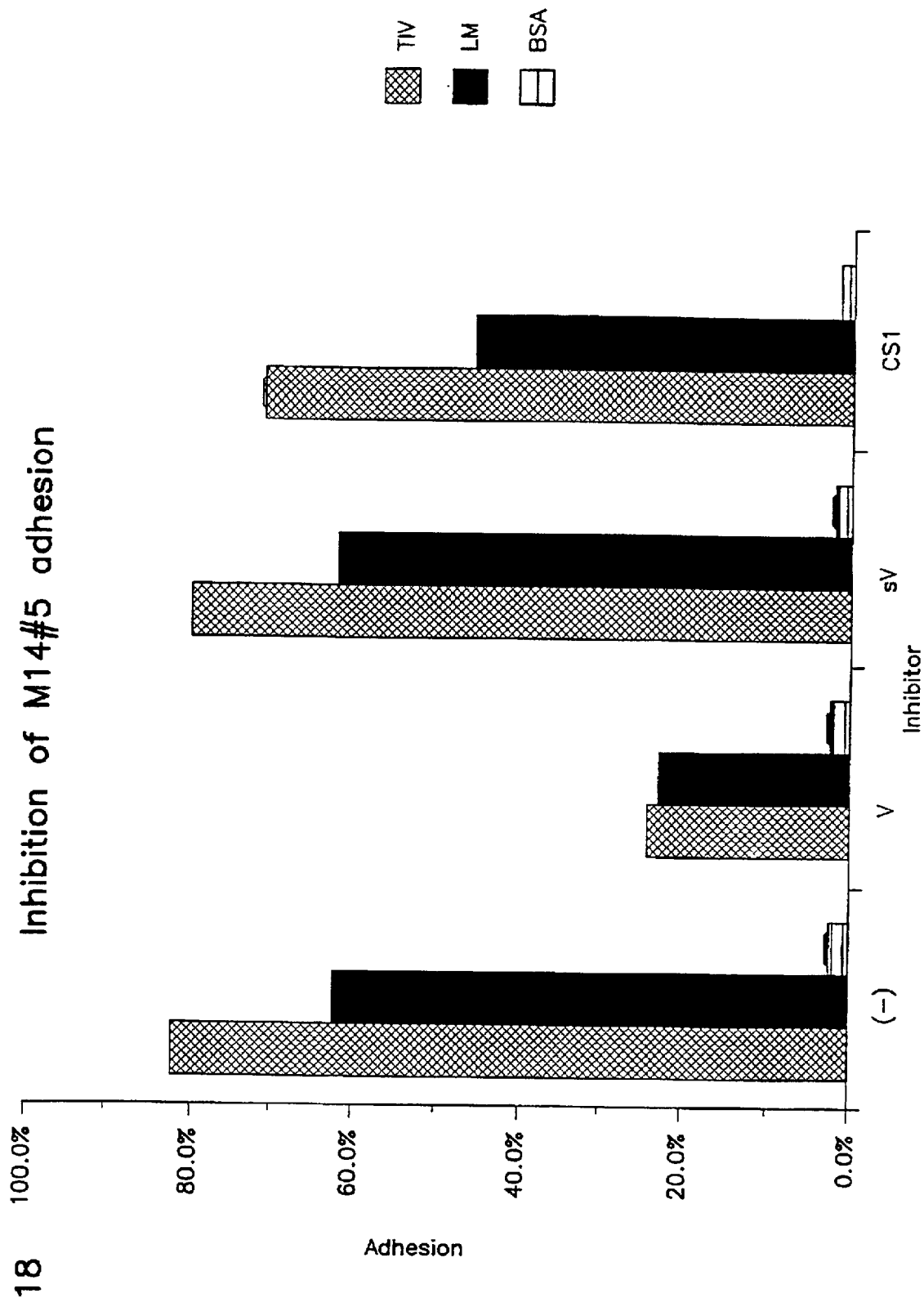
FIG. 18 shows a graph of % adhesion of the α2β1, α3β1 integrin dependent human melanoma M14#5 cell adhesion to laminin ("LM") and type IV collagen ("TIV") and bovine serum albumin ("BSA").

Soluble peptide FN-C/H V inhibited human melanoma M14#5 cell adhesion to laminin and type IV collagen coated substrates, whereas scrambled FN-C/H V has no effect (see FIG. 18). This adhesion is dependent on α2β1 and α3β1 integrin as determined using specific anti-integrin blocking mAbs (data not shown).

Example 13
Influence of Chirality on Inhibition of α4β1 Integrin Dependent Adhesion The potential chiral dependence of β1 integrin dependent cell adhesion by the present peptides was examined by preparing the all D-form of FN-C/H V+Y (SEQ ID NO:1) and the all L-form of retro inverso FN-C/H V+Y (SEQ ID NO:40; the all L-form of YIRARPPQW, the reverse primary sequence of FN-C/H V+Y). These two compounds were examined in the 8A2 stimulated Ramos cell adhesion assay.

Figure 19:
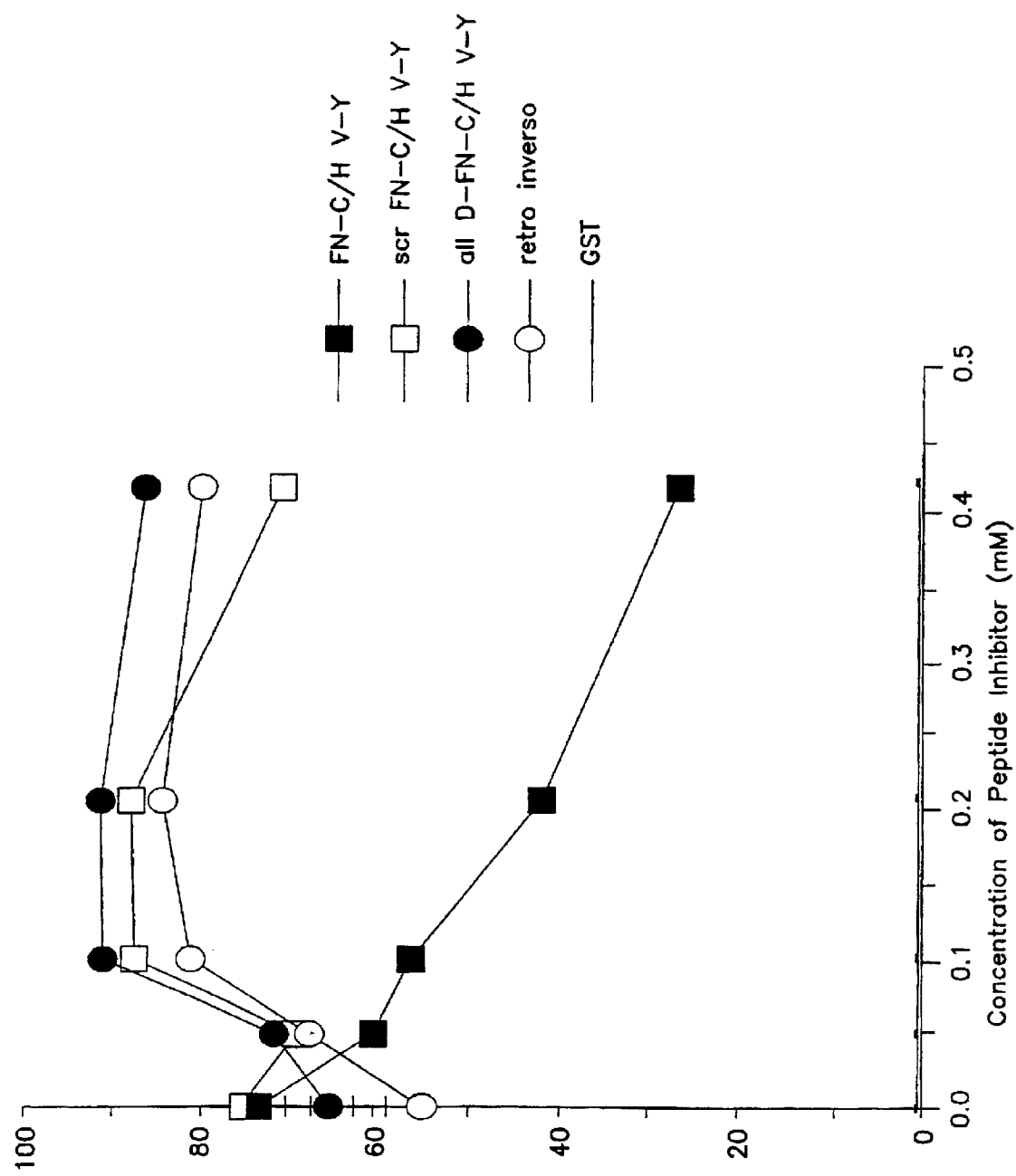
FIG. 19 shows a graph of % adhesion of 8A2 stimulated Ramos cells to IIICS-GST as a function of the concentration of all D-FN C/H V+Y (SEQ ID NO: 1), and a retro inverso form of FN C/H V+Y (SEQ ID NO:40) versus various controls.

The results (shown in FIG. 19) show that there is a chiral dependence on the adhesion inhibitory activity of FN-C/H V–Y. This suggests that C-terminal isoleucine-tyrosine should be in the L-enantiomeric form since D-amino acid FN-C/H V–Y and a retro-inverso FN-C/H V–Y (consisting of the L-amino acids in reverse primary sequence) are both unable to inhibit adhesion.

Ramos cells and the β1 integrin stimulatory mAb 8A2 were preincubated with the indicated concentration of synthetic peptide prior to addition to rCS1 coated wells. (V), (sV) represent peptides FN-C/H V–Y and scrambled FN-C/H V–Y, respectively. Each data point represents the mean of triplicate determinations and the error bars represent standard deviation of the mean. Background Ramos adhesion to GST is represented in the solid black line.

Example 14
Inhibition of α1β2 Integrin Dependent Adhesion

To determine whether inhibition of adhesion by soluble FN-C/H V is specific for b1 integrins, the ability of this peptide to inhibit β2 integrin-dependent adhesion was also evaluated. For these studies the adhesion of the B-cell line M16B (which both express functional α4β1 and α1β2 integrin) to purified rCS 1 or recombinatnt ICAM in the presence of soluble FN-C/H V. As expected, α4β1 integrin-dependent $Mn^{+2}$ stimulated M16B adhesion to rCS1 was completely inhibited by soluble FN-C/H V and CS1. However, α1β2 (LFA-1) integrin dependent adhesion to rICAM was not inhibited by soluble FN-C/H V, although this adhesion can be inhibited by an anti-β2 integrin blocking mAb.

The invention has been described with reference to various specific and preferred embodiments and techniques. However, it should be understood that many variations and modifications may be made while remaining within the spirit and scope of the invention.

TABLE I

| | Peptide Sequences | |
|---|---|---|
| SEQ ID NO: | Amino Acid Sequence | Net Charge |
| 2 | RPQIPWARY | +2 |
| 3 | AQPPRARIY | +2 |

TABLE I-continued

Peptide Sequences

| SEQ ID NO: | Amino Acid Sequence | Net Charge |
|---|---|---|
| 4 | WAPPRARIY | +2 |
| 5 | WQAPRARIY | +2 |
| 6 | WQPARARIY | +2 |
| 7 | WQPPAARIY | +1 |
| 8 | WQPPRAAIY | +1 |
| 9 | WQPPRARAY | +2 |
| 10 | QPPRARITY | +2 |
| 11 | PPRARITGY | +2 |
| 12 | PRARITGYY | +2 |
| 13 | RARITGYIY | +2 |
| 14 | ARITGYIIY | +1 |
| 15 | RITGYIIKY | 0 |
| 16 | ITGYIIKYY | −1 |
| 17 | PRQAWRPI | +2 |
| 18 | PRQAWRPIY | +2 |
| 19 | RPAPQRWI | +2 |
| 20 | RPAPQRWIY | +2 |
| 21 | ARITGYII | +1 |
| 22 | QPPRARIY | +2 |
| 23 | PPRARIY | +2 |
| 24 | PRARIY | +2 |
| 25 | RARIY | +2 |
| 26 | ARIY | +1 |
| 27 | WQPPRARKY | +1 |
| 28 | WQPPRARLY | +2 |
| 29 | WQPPRARVY | +2 |
| 30 | WQPPRARTY | +2 |
| 31 | WQPPRARMY | +2 |
| 32 | WQPPRARIF | +2 |
| 33 | WQPPRARIW | +2 |
| 34 | IYWQPPRAR | +2 |
| 35 | WQPIYPRAR | +2 |
| 36 | WQPPRARYI | +2 |
| 37 | WQPPRARI | +2 |
| 38 | WQPPDADIY | −2 |
| 39 | PRARI | +2 |
| 40 | YIRARPPQW | +2 |

What is claimed is:

1. A peptide of no more than about six amino acid residues, said peptide having the sequence Pro-Arg-Ala-Arg-Ile-Tyr (SEQ ID NO:24), Arg-Ala-Arg-Ile-Tyr (SEQ ID NO:25), Ala-Arg-Ile-Tyr (SEQ ID NO:26), or Arg-Ile-Tyr, wherein said peptide retains a C-terminal Ile-Tyr dipeptide sequence.

2. The peptide of claim 1 wherein said peptide inhibits β1 integrin subunit dependent adhesion.

3. The peptide of claim 2 wherein said peptide inhibits α5β1 integrin dependent cell adhesion.

4. The peptide of claim 2 wherein said peptide inhibits α4β1 integrin dependent adhesion.

5. The peptide of claim 4 wherein said peptide inhibits α4β1 integrin dependent adhesion of Ramos cells to α4β1 integrin binding fibronectin fragments.

6. A method for inhibiting the β1 integrin subunit dependent adhesion of cells to a substrate, the method comprising:

combining a peptide of claim 1 with a suspension of said cells to form a modified cell suspension; and contacting the modified cell suspension with the substrate; wherein the β1 integrin subunit dependent adhesion of said cells to a substrate is inhibited.

7. The method of claim 6 wherein the β1 integrin is α4β1.

8. The method of claim 6 wherein the β1 integrin is α5β1.

9. A method of inhibiting α4β1 integrin dependent adhesion of cells to integrin-binding fibronectin fragments, the method comprising:

combining a peptide of claim 6 with the cells to form a modified cell suspension; and contacting the modified cell suspension with the integrin-binding fibronectin fragments;

wherein α4β1 integrin dependent adhesion of the cells of the modified cell suspension to integrin-binding fibronectin fragments is inhibited.

10. A peptide consisting of the sequence Pro-Arg-Ala-Arg-Ile-Tyr (SEQ ID NO:24), Arg-Ala-Arg-Ile-Tyr (SEQ ID NO:25), Ala-Arg-Ile-Tyr (SEQ ID NO:26), or Arg-Ile-Tyr.

11. The peptide of claim 10 wherein said peptide inhibits β1 integrin subunit dependent adhesion.

12. The peptide of claim 11 wherein said peptide inhibits α4β1 integrin dependent adhesion.

13. The peptide of claim 12 wherein said peptide inhibits α4β1 integrin dependent adhesion of Ramos cells to α4β1 integrin binding fibronectin fragments.

14. The peptide of claim 11 wherein said peptide inhibits α5β1 integrin dependent cell adhesion.

15. A method of inhibiting α4β1 integrin dependent adhesion of cells to integrin-binding fibronectin fragments, the method comprising:

combining a peptide of claim 10 with the cells to form a modified cell suspension; and contacting the modified cell suspension with the integrin-binding fibronectin fragments;

wherein α4β1 integrin dependent adhesion of the cells of the modified cell suspension to integrin-binding fibronectin fragments is inhibited.

16. A method for inhibiting the β1 integrin subunit dependent adhesion of cells to a substrate, the method comprising:

combining a peptide of claim 10 with a suspension of said cells to form a modified cell suspension; and contacting the modified cell suspension with the substrate; wherein the β1 integrin subunit dependent adhesion of said cells to a substrate is inhibited.

17. The method of claim 16 wherein the β1 integrin is α4β1.

18. The method of claim 16 wherein the β1 integrin is α5β1.

19. A peptide of no more than about ten amino acid residues, said peptide having the sequence Pro-Arg-Ala-Arg-Ile-Tyr (SEQ ID NO:24), Arg-Ala-Arg-Ile-Tyr (SEQ ID NO:25), or Ala-Arg-Ile-Tyr (SEQ ID NO:26), wherein said peptide retains a C-terminal Ile-Tyr dipeptide sequence.

20. The peptide of claim 19 wherein said peptide inhibits α1 integrin subunit dependent adhesion.

21. The peptide of claim 20 wherein said peptide inhibits α4β1 integrin dependent adhesion.

22. The peptide of claim 21 wherein said peptide inhibits α4β1 integrin dependent adhesion of Ramos cells to α4β1 integrin binding fibronectin fragments.

23. The peptide of claim 20 wherein said peptide inhibits α5β1 integrin dependent cell adhesion.

24. A method of inhibiting α4β1 integrin dependent adhesion of cells to integrin-binding fibronectin fragments, the method comprising:

combining a peptide of claim 19 with the cells to form a modified cell suspension; and contacting the modified cell suspension with the integrin-binding fibronectin fragments;

wherein α4β1 integrin dependent adhesion of the cells of the modified cell suspension to integrin-binding fibronectin fragments is inhibited.

25. A method for inhibiting the β1 integrin subunit dependent adhesion of cells to a substrate, the method comprising:

combining a peptide of claim 19 with a suspension of said cells to form a modified cell suspension; and contacting the modified cell suspension with the substrate; wherein the β1 integrin subunit dependent adhesion of said cells to a substrate is inhibited.

26. The method of claim 25 wherein the β1 integrin is α4β1.

27. The method of claim 25 wherein the β1 integrin is α5β1.

* * * * *

UNITED STATES PATENT AND TRADEMARK OFFICE
CERTIFICATE OF CORRECTION

PATENT NO. : 6,849,712 B1
DATED : February 1, 2005
INVENTOR(S) : McCarthy et al.

It is certified that error appears in the above-identified patent and that said Letters Patent is hereby corrected as shown below:

<u>Title page,</u>
Item [56], References Cited, U.S. PATENT DOCUMENTS, insert -- 4,839,464 * 6/1989 McCarthy et al. ......530/326
    4,923,963 * 5/1990 Stewart et al. ..........530/314
    4,938,949 * 7/1990 Borch et al. .............514/476
    5,019,646 * 5/1991 Furcht et al. ...........530/326
    5,147,797 * 9/1992 McCarthy et al. .....435/398
    5,171,271 * 12/1992 Furcht et al. ...........623/23.76
    5,278,063 * 1/1994 Hubbell et al. .........435/402
    5,294,551 * 3/1994 Furcht et al. ...........435/402
    5,330,911 * 7/1994 Hubbell et al. .........435/402
    5,380,668 * 1/1995 Herron, James N. ...436/510
    5,545,620 * 8/1996 Wahl et al. ..............514/12
    5,591,719 * 1/1997 Furcht et al. ............514/13
    5,595,887 * 1/1997 Coolidge et al. ........435/69.7
    5,710,123 * 1/1998 Heavner et al. .........514/2
    5,744,515 * 4/1998 Clapper, David L. ..523/113
    5,840,691 * 11/1998 Furcht et al. ............514/12
    5,846,536 * 12/1998 Bissell et al. ............424/158.1
    5,853,744 * 12/1998 Mooradian et al. .....424/422
    6,110,895 * 8/2000 Rodgers et al. .........514/15--

FOREIGN PATENT DOCUMENTS, insert

-- WO 97/23451 07/1997
   WO 97/34617 09/1997

WO 97/30070 08/1997
   WO 98/00395 01/1998
   WO 99/37669 07/1999
   WO 00/56350 09/2000-- .

OTHER PUBLICATIONS, insert

-- Carraway, R.E. Peptides (New York, NY, United States) 14(1), 37-45, 1993*

Qi, Jie, Shengwu Huaxue Zazhi 13(5), 576-579, 1997*

Chappell et al., "Inhibition of Leukocyte-Mediated Tissue Destruction by Synthetic Fibronectin Peptide (Trp-9-Tyr), "Journal of Burn Care and Rehabilitation, 20((6):505-510 (November, 1999); presented at 31st Annual Meeting, American Burn Association, March 24-27, Lake Buena Vista, FL., (March 25, 1999)

English Abstract of JP 6016568, 01/25/1994

English Abstract of Seki et al., (J. Jap. Soc. Food Sci. Technol., 43, 967, 1996)

Nwariaku et al., "Inhibition of Selectin- and Integrin-Mediated Inflammatory Response after Burn Injury" Journal of Surgical Research, 63(1):355-358 (1996)--

UNITED STATES PATENT AND TRADEMARK OFFICE
CERTIFICATE OF CORRECTION

PATENT NO. : 6,849,712 B1
DATED : February 1, 2005
INVENTOR(S) : McCarthy et al.

It is certified that error appears in the above-identified patent and that said Letters Patent is hereby corrected as shown below:

Title page (cont'd),
OTHER PUBLICATIONS,
"Lasz et al." reference, delete "$62_3$" and insert -- $\beta_3$ --.

Column 7,
Line 11, delete "peptidelcarrier" and insert -- peptide/carrier --.

Column 8,
Line 8, delete "Tl/well" and insert -- $\mu$l/well --.
Line 9, delete "Tg/ml" and insert -- $\mu$g/well --.
Line 12, delete "$\mu$/well" and insert -- $\mu$l/well --.

Column 10,
Line 23, delete "NO:29" and insert -- NO:28 --.

Column 27,
Line 12, delete "about".

Column 28,
Line 26, delete "about".
Line 32, delete "$\alpha$1" and insert -- $\beta$1 --.

Signed and Sealed this

Twenty-third Day of August, 2005

JON W. DUDAS
*Director of the United States Patent and Trademark Office*

SEQUENCE LISTING

```
<160> NUMBER OF SEQ ID NOS: 46

<210> SEQ ID NO 1
<211> LENGTH: 9
<212> TYPE: PRT
<213> ORGANISM: Homo sapiens

<400> SEQUENCE: 1

Trp Gln Pro Pro Arg Ala Arg Ile Tyr
 1               5

<210> SEQ ID NO 2
<211> LENGTH: 9
<212> TYPE: PRT
<213> ORGANISM: Homo sapiens

<400> SEQUENCE: 2

Arg Pro Gln Ile Pro Trp Ala Arg Tyr
 1               5

<210> SEQ ID NO 3
<211> LENGTH: 9
<212> TYPE: PRT
<213> ORGANISM: Homo sapiens

<400> SEQUENCE: 3

Ala Gln Pro Pro Arg Ala Arg Ile Tyr
 1               5
```

```
<210> SEQ ID NO 4
<211> LENGTH: 9
<212> TYPE: PRT
<213> ORGANISM: Homo sapiens

<400> SEQUENCE: 4

Trp Ala Pro Pro Arg Ala Arg Ile Tyr
 1               5

<210> SEQ ID NO 5
<211> LENGTH: 9
<212> TYPE: PRT
<213> ORGANISM: Homo sapiens

<400> SEQUENCE: 5

Trp Gln Ala Pro Arg Ala Arg Ile Tyr
 1               5

<210> SEQ ID NO 6
<211> LENGTH: 9
<212> TYPE: PRT
<213> ORGANISM: Homo sapiens

<400> SEQUENCE: 6

Trp Gln Pro Ala Arg Ala Arg Ile Tyr
 1               5

<210> SEQ ID NO 7
<211> LENGTH: 9
<212> TYPE: PRT
<213> ORGANISM: Homo sapiens

<400> SEQUENCE: 7

Trp Gln Pro Pro Ala Ala Arg Ile Tyr
 1               5

<210> SEQ ID NO 8
<211> LENGTH: 9
<212> TYPE: PRT
<213> ORGANISM: Homo sapiens

<400> SEQUENCE: 8

Trp Gln Pro Pro Arg Ala Ala Ile Tyr
 1               5

<210> SEQ ID NO 9
<211> LENGTH: 9
<212> TYPE: PRT
<213> ORGANISM: Homo sapiens

<400> SEQUENCE: 9

Trp Gln Pro Pro Arg Ala Arg Ala Tyr
 1               5

<210> SEQ ID NO 10
<211> LENGTH: 9
<212> TYPE: PRT
<213> ORGANISM: Homo sapiens

<400> SEQUENCE: 10

Gln Pro Pro Arg Ala Arg Ile Thr Tyr
 1               5

<210> SEQ ID NO 11
```

```
<211> LENGTH: 9
<212> TYPE: PRT
<213> ORGANISM: Homo sapiens

<400> SEQUENCE: 11

Pro Pro Arg Ala Arg Ile Thr Gly Tyr
 1               5

<210> SEQ ID NO 12
<211> LENGTH: 9
<212> TYPE: PRT
<213> ORGANISM: Homo sapiens

<400> SEQUENCE: 12

Pro Arg Ala Arg Ile Thr Gly Tyr Tyr
 1               5

<210> SEQ ID NO 13
<211> LENGTH: 9
<212> TYPE: PRT
<213> ORGANISM: Homo sapiens

<400> SEQUENCE: 13

Arg Ala Arg Ile Thr Gly Tyr Ile Tyr
 1               5

<210> SEQ ID NO 14
<211> LENGTH: 9
<212> TYPE: PRT
<213> ORGANISM: Homo sapiens

<400> SEQUENCE: 14

Ala Arg Ile Thr Gly Tyr Ile Ile Tyr
 1               5

<210> SEQ ID NO 15
<211> LENGTH: 9
<212> TYPE: PRT
<213> ORGANISM: Homo sapiens

<400> SEQUENCE: 15

Arg Ile Thr Gly Tyr Ile Ile Lys Tyr
 1               5

<210> SEQ ID NO 16
<211> LENGTH: 9
<212> TYPE: PRT
<213> ORGANISM: Homo sapiens

<400> SEQUENCE: 16

Ile Thr Gly Tyr Ile Ile Lys Tyr Tyr
 1               5

<210> SEQ ID NO 17
<211> LENGTH: 8
<212> TYPE: PRT
<213> ORGANISM: Homo sapiens

<400> SEQUENCE: 17

Pro Arg Gln Ala Trp Arg Pro Ile
 1               5

<210> SEQ ID NO 18
<211> LENGTH: 9
<212> TYPE: PRT
```

```
<213> ORGANISM: Homo sapiens

<400> SEQUENCE: 18

Pro Arg Gln Ala Trp Arg Pro Ile Tyr
 1               5

<210> SEQ ID NO 19
<211> LENGTH: 8
<212> TYPE: PRT
<213> ORGANISM: Homo sapiens

<400> SEQUENCE: 19

Arg Pro Ala Pro Gln Arg Trp Ile
 1               5

<210> SEQ ID NO 20
<211> LENGTH: 9
<212> TYPE: PRT
<213> ORGANISM: Homo sapiens

<400> SEQUENCE: 20

Arg Pro Ala Pro Gln Arg Trp Ile Tyr
 1               5

<210> SEQ ID NO 21
<211> LENGTH: 8
<212> TYPE: PRT
<213> ORGANISM: Homo sapiens

<400> SEQUENCE: 21

Ala Arg Ile Thr Gly Tyr Ile Ile
 1               5

<210> SEQ ID NO 22
<211> LENGTH: 8
<212> TYPE: PRT
<213> ORGANISM: Homo sapiens

<400> SEQUENCE: 22

Gln Pro Pro Arg Ala Arg Ile Tyr
 1               5

<210> SEQ ID NO 23
<211> LENGTH: 7
<212> TYPE: PRT
<213> ORGANISM: Homo sapiens

<400> SEQUENCE: 23

Pro Pro Arg Ala Arg Ile Tyr
 1               5

<210> SEQ ID NO 24
<211> LENGTH: 6
<212> TYPE: PRT
<213> ORGANISM: Homo sapiens

<400> SEQUENCE: 24

Pro Arg Ala Arg Ile Tyr
 1               5

<210> SEQ ID NO 25
<211> LENGTH: 5
<212> TYPE: PRT
<213> ORGANISM: Homo sapiens
```

-continued

```
<400> SEQUENCE: 25

Arg Ala Arg Ile Tyr
1               5

<210> SEQ ID NO 26
<211> LENGTH: 4
<212> TYPE: PRT
<213> ORGANISM: Homo sapiens

<400> SEQUENCE: 26

Ala Arg Ile Tyr
1

<210> SEQ ID NO 27
<211> LENGTH: 9
<212> TYPE: PRT
<213> ORGANISM: Homo sapiens

<400> SEQUENCE: 27

Trp Gln Pro Pro Arg Ala Arg Lys Tyr
1               5

<210> SEQ ID NO 28
<211> LENGTH: 9
<212> TYPE: PRT
<213> ORGANISM: Homo sapiens

<400> SEQUENCE: 28

Trp Gln Pro Pro Arg Ala Arg Leu Tyr
1               5

<210> SEQ ID NO 29
<211> LENGTH: 9
<212> TYPE: PRT
<213> ORGANISM: Homo sapiens

<400> SEQUENCE: 29

Trp Gln Pro Pro Arg Ala Arg Val Tyr
1               5

<210> SEQ ID NO 30
<211> LENGTH: 9
<212> TYPE: PRT
<213> ORGANISM: Homo sapiens

<400> SEQUENCE: 30

Trp Gln Pro Pro Arg Ala Arg Thr Tyr
1               5

<210> SEQ ID NO 31
<211> LENGTH: 9
<212> TYPE: PRT
<213> ORGANISM: Homo sapiens

<400> SEQUENCE: 31

Trp Gln Pro Pro Arg Ala Arg Met Tyr
1               5

<210> SEQ ID NO 32
<211> LENGTH: 9
<212> TYPE: PRT
<213> ORGANISM: Homo sapiens

<400> SEQUENCE: 32
```

Trp Gln Pro Pro Arg Ala Arg Ile Phe
1               5

<210> SEQ ID NO 33
<211> LENGTH: 9
<212> TYPE: PRT
<213> ORGANISM: Homo sapiens

<400> SEQUENCE: 33

Trp Gln Pro Pro Arg Ala Arg Ile Trp
1               5

<210> SEQ ID NO 34
<211> LENGTH: 9
<212> TYPE: PRT
<213> ORGANISM: Homo sapiens

<400> SEQUENCE: 34

Ile Tyr Trp Gln Pro Pro Arg Ala Arg
1               5

<210> SEQ ID NO 35
<211> LENGTH: 9
<212> TYPE: PRT
<213> ORGANISM: Homo sapiens

<400> SEQUENCE: 35

Trp Gln Pro Ile Tyr Pro Arg Ala Arg
1               5

<210> SEQ ID NO 36
<211> LENGTH: 9
<212> TYPE: PRT
<213> ORGANISM: Homo sapiens

<400> SEQUENCE: 36

Trp Gln Pro Pro Arg Ala Arg Tyr Ile
1               5

<210> SEQ ID NO 37
<211> LENGTH: 8
<212> TYPE: PRT
<213> ORGANISM: Homo sapiens

<400> SEQUENCE: 37

Trp Gln Pro Pro Arg Ala Arg Ile
1               5

<210> SEQ ID NO 38
<211> LENGTH: 9
<212> TYPE: PRT
<213> ORGANISM: Homo sapiens

<400> SEQUENCE: 38

Trp Gln Pro Pro Asp Ala Asp Ile Tyr
1               5

<210> SEQ ID NO 39
<211> LENGTH: 5
<212> TYPE: PRT
<213> ORGANISM: Homo sapiens

<400> SEQUENCE: 39

Pro Arg Ala Arg Ile
1               5

<210> SEQ ID NO 40
<211> LENGTH: 9
<212> TYPE: PRT
<213> ORGANISM: Homo sapiens

<400> SEQUENCE: 40

Tyr Ile Arg Ala Arg Pro Pro Gln Trp
 1               5

<210> SEQ ID NO 41
<211> LENGTH: 10
<212> TYPE: PRT
<213> ORGANISM: Homo sapiens

<400> SEQUENCE: 41

Pro Ala Ile Phe Asp Arg Ser Cys Gly Ser
 1               5                  10

<210> SEQ ID NO 42
<211> LENGTH: 20
<212> TYPE: PRT
<213> ORGANISM: Homo sapiens

<400> SEQUENCE: 42

Tyr Glu Lys Pro Gly Ser Pro Pro Arg Glu Val Val Pro Arg Pro Arg
 1               5                  10                  15

Pro Gly Val Tyr
            20

<210> SEQ ID NO 43
<211> LENGTH: 16
<212> TYPE: PRT
<213> ORGANISM: Homo sapiens

<400> SEQUENCE: 43

Lys Asn Asn Gln Lys Ser Glu Pro Leu Ile Gly Arg Lys Lys Thr Tyr
 1               5                  10                  15

<210> SEQ ID NO 44
<211> LENGTH: 10
<212> TYPE: PRT
<213> ORGANISM: Homo sapiens

<400> SEQUENCE: 44

Ser Pro Pro Arg Arg Ala Arg Val Thr Tyr
 1               5                  10

<210> SEQ ID NO 45
<211> LENGTH: 10
<212> TYPE: PRT
<213> ORGANISM: Homo sapiens

<400> SEQUENCE: 45

Pro Lys Val Met Glu Arg Thr Cys Asp Ser
 1               5                  10

<210> SEQ ID NO 46
<211> LENGTH: 25
<212> TYPE: PRT
<213> ORGANISM: Homo sapiens

<400> SEQUENCE: 46

-continued

```
Asp Glu Leu Pro Gln Leu Val Thr Leu Pro His Pro Asn Leu His Gly
 1               5                  10                  15

Pro Glu Ile Leu Asp Val Pro Ser Thr
            20              25
```